US010195584B2

(12) United States Patent
Tachi et al.

(10) Patent No.: US 10,195,584 B2
(45) Date of Patent: Feb. 5, 2019

(54) WATER ABSORBENT RESIN MATERIAL, AND METHOD FOR PRODUCING SAME

(71) Applicant: NIPPON SHOKUBAI CO., LTD., Osaka (JP)

(72) Inventors: Koji Tachi, Himeji (JP); Hironori Sato, Himeji (JP); Kazushi Torii, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 322 days.

(21) Appl. No.: 14/763,912

(22) PCT Filed: Jan. 28, 2014

(86) PCT No.: PCT/JP2014/051794
§ 371 (c)(1),
(2) Date: Jul. 28, 2015

(87) PCT Pub. No.: WO2014/119553
PCT Pub. Date: Aug. 7, 2014

(65) Prior Publication Data
US 2015/0360204 A1 Dec. 17, 2015

(30) Foreign Application Priority Data

Jan. 29, 2013 (JP) ................. 2013-014296

(51) Int. Cl.
*B01J 20/26* (2006.01)
*C08L 101/14* (2006.01)
*C08J 3/24* (2006.01)
*A61L 15/24* (2006.01)
*A61L 15/60* (2006.01)
*B01J 20/30* (2006.01)

(52) U.S. Cl.
CPC ............ *B01J 20/261* (2013.01); *A61L 15/24* (2013.01); *A61L 15/60* (2013.01); *B01J 20/267* (2013.01); *B01J 20/3078* (2013.01); *B01J 20/3085* (2013.01); *C08J 3/245* (2013.01); *C08L 101/14* (2013.01); *C08J 2300/14* (2013.01); *C08J 2333/02* (2013.01)

(58) Field of Classification Search
CPC .... B01J 20/261; B01J 20/3085; B01J 20/267; B01J 20/3078; A61L 15/24; A61L 15/60; C08J 3/245; C08J 2300/14; C08J 2333/02; C08L 101/14
USPC ........................................................ 502/402
See application file for complete search history.

(56) References Cited

U.S. PATENT DOCUMENTS

| 4,824,901 | A | 4/1989 | Alexander et al. |
| 5,300,602 | A * | 4/1994 | Arita ..................... C08F 226/06 524/549 |
| 5,382,610 | A | 1/1995 | Harada et al. |
| 5,728,742 | A | 3/1998 | Staples et al. |
| 6,297,319 | B1 | 10/2001 | Nagasuna et al. |
| 6,300,275 | B1 | 10/2001 | Weir |
| 6,605,673 | B1 | 8/2003 | Mertens et al. |
| 6,620,889 | B1 | 9/2003 | Mertens et al. |
| 2003/0207997 | A1 | 11/2003 | Mertens et al. |
| 2004/0071966 | A1 | 4/2004 | Inger et al. |
| 2004/0157734 | A1 | 8/2004 | Mertens et al. |
| 2004/0176557 | A1 | 9/2004 | Mertens et al. |
| 2004/0214499 | A1 | 10/2004 | Qin et al. |
| 2004/0214946 | A1 | 10/2004 | Smith et al. |
| 2005/0020780 | A1 | 1/2005 | Inger et al. |
| 2005/0096435 | A1 | 5/2005 | Smith et al. |
| 2005/0113252 | A1 | 5/2005 | Miyake et al. |
| 2005/0215966 | A1 | 9/2005 | Borgmann et al. |
| 2005/0245684 | A1 | 11/2005 | Daniel et al. |
| 2005/0256469 | A1 | 11/2005 | Qin et al. |
| 2007/0066718 | A1 | 3/2007 | Smith et al. |
| 2007/0129495 | A1 | 6/2007 | Mertens et al. |
| 2007/0167560 | A1 | 7/2007 | Smith et al. |
| 2007/0244283 | A1 | 10/2007 | Riegel et al. |
| 2008/0114129 | A1 | 5/2008 | Herfert et al. |
| 2008/0124551 | A1 | 5/2008 | Daniel et al. |
| 2008/0154224 | A1 | 6/2008 | Daniel et al. |
| 2008/0187756 | A1 | 8/2008 | Riegel et al. |
| 2008/0200331 | A1 | 8/2008 | Daniel et al. |
| 2008/0221229 | A1 | 9/2008 | Torii et al. |
| 2008/0221277 | A1 | 9/2008 | Walden et al. |
| 2008/0234420 | A1 | 9/2008 | Smith et al. |
| 2008/0234645 | A1 | 9/2008 | Dodge et al. |
| 2008/0280128 | A1 | 11/2008 | Furno et al. |
| 2009/0023848 | A1 | 1/2009 | Ahmed et al. |
| 2009/0105389 | A1 | 4/2009 | Walden et al. |
| 2009/0202805 | A1 | 8/2009 | Furno et al. |
| 2009/0227741 | A1 | 9/2009 | Walden et al. |
| 2010/0019198 | A1 | 1/2010 | Stueven et al. |
| 2010/0041550 | A1 | 2/2010 | Riegel et al. |

(Continued)

FOREIGN PATENT DOCUMENTS

JP  05-031362 A  2/1993
JP  2000-197818 A  7/2000

(Continued)

OTHER PUBLICATIONS

Supplementary European Search Report dated Aug. 2, 2016, issued in a corresponding EP Patent Application No. 14746833.4.

(Continued)

*Primary Examiner* — Haytham Soliman
(74) *Attorney, Agent, or Firm* — Dickinson Wright PLLC

(57) ABSTRACT

An object of the present invention is to provide a water absorbent resin which attains high liquid permeability and water absorbing speed, and which does not have problems of coloring and odor. The water absorbent resin includes: (A) a water absorbent resin particle having a carboxyl group; (B) a covalent surface crosslinking agent in which the number of carbons is not more than 10; (C) 0.001 mass % to 0.2 mass % of a water-soluble or water-dispersible polymer whose Log P is not less than 1.0; and (D) 0.001 mass % to 1 mass % of a water-soluble polyvalent cation. The water absorbent resin has not less than 20 g/g of a fixed height absorption (FHA) at a height of 20 cm.

15 Claims, No Drawings

(56) References Cited

U.S. PATENT DOCUMENTS

| | | |
|---|---|---|
| 2010/0184594 A1 | 7/2010 | Riegel et al. |
| 2010/0190932 A1 | 7/2010 | Riegel et al. |
| 2010/0247916 A1 | 9/2010 | Hamilton et al. |
| 2010/0261812 A1 | 10/2010 | Qin et al. |
| 2010/0279860 A1 | 11/2010 | Smith et al. |
| 2010/0294988 A1 | 11/2010 | Stueven et al. |
| 2010/0311578 A1 | 12/2010 | Smith et al. |
| 2011/0003926 A1* | 1/2011 | Nogi .................. B65B 1/08 524/401 |
| 2011/0006140 A1 | 1/2011 | Ishizaki et al. |
| 2011/0009590 A1 | 1/2011 | Matsumoto et al. |
| 2011/0009841 A1 | 1/2011 | Ahmed et al. |
| 2011/0011491 A1 | 1/2011 | Matsumoto et al. |
| 2011/0015351 A1 | 1/2011 | Nogi et al. |
| 2011/0028670 A1 | 2/2011 | Matsumoto et al. |
| 2011/0088806 A1 | 4/2011 | Nogi et al. |
| 2011/0110730 A1 | 5/2011 | Nogi et al. |
| 2011/0166300 A1 | 7/2011 | Dairoku et al. |
| 2011/0180755 A1 | 7/2011 | Adachi et al. |
| 2012/0083411 A1 | 4/2012 | Ahmed et al. |
| 2012/0277096 A1 | 11/2012 | Smith et al. |
| 2013/0310251 A1 | 11/2013 | Smith et al. |
| 2014/0031473 A1 | 1/2014 | Nogi et al. |
| 2014/0031498 A1 | 1/2014 | Smith et al. |
| 2014/0042364 A1 | 2/2014 | Nogi et al. |
| 2014/0350191 A1 | 11/2014 | Walden et al. |

FOREIGN PATENT DOCUMENTS

| | | |
|---|---|---|
| JP | 2000-509081 | 7/2000 |
| JP | 2001-523289 A | 11/2001 |
| JP | 2002-226599 | 8/2002 |
| JP | 2004-315613 | 11/2004 |
| JP | 2005-095759 A | 4/2005 |
| JP | 2005-097604 | 4/2005 |
| JP | 2006-089734 | 4/2006 |
| JP | 2006-524541 A | 11/2006 |
| JP | 2006-526691 A | 11/2006 |
| JP | 2007-510045 A | 4/2007 |
| JP | 2007-529292 A | 10/2007 |
| JP | 2007-530752 A | 11/2007 |
| JP | 2008-528751 A | 7/2008 |
| JP | 2008-538121 A | 10/2008 |
| JP | 2009-534483 A | 9/2009 |
| JP | 2010-513631 A | 4/2010 |
| JP | 2010-513632 A | 4/2010 |
| JP | 2010-522008 A | 7/2010 |
| JP | 2010-522255 A | 7/2010 |
| JP | 2010-533766 A | 10/2010 |
| JP | 2010-534751 A | 11/2010 |
| JP | 2010-534752 A | 11/2010 |
| JP | 2010-540206 A | 12/2010 |
| WO | WO 2000/053644 | 9/2000 |
| WO | WO 2001/74913 A1 | 10/2001 |
| WO | WO 2007/121937 A2 | 11/2007 |
| WO | WO 2008/092843 A1 | 8/2008 |
| WO | WO 2008/108343 A1 | 9/2008 |
| WO | WO 2009/080611 A2 | 7/2009 |
| WO | WO 2009/113671 A1 | 9/2009 |
| WO | WO 2010/108875 A1 | 9/2010 |
| WO | WO 2012/102406 A1 | 8/2012 |
| WO | WO 2012/102407 A1 | 8/2012 |

OTHER PUBLICATIONS

International Search Report issued by Japanese Patent Office in PCT Patent Application No. SPCT/JP2014/051794, dated Aug. 4, 2015, including English translation.

PCT International Preliminary Report on Patentability and Written Opinion of the International Searching Authority issued by the International Bureau of WIPO in PCT/JP2014/051794 dated Aug. 4, 2015, 8 pages.

International Search Report for PCT/JP2014/051794, dated Apr. 1, 2014, and English translation thereof.

* cited by examiner

WATER ABSORBENT RESIN MATERIAL, AND METHOD FOR PRODUCING SAME

TECHNICAL FIELD

The present invention relates to a water absorbent resin material, and a method for producing the water absorbent resin material. The present invention particularly relates to (i) a water absorbent resin material suitably applicable to, for example, hygienic materials such as disposable diapers, sanitary napkins, and so-called incontinence pads, and (ii) a method for producing the water absorbent resin material.

BACKGROUND ART

A water absorbent resin (SAP/Super Absorbent Polymer) is a water-swelling and water-insoluble polymer gelatinizer, and is used mainly for disposable purpose, i.e., for absorbent articles such as disposable diapers and sanitary napkins, and for an agriculture/horticulture water retention agent, an industrial waterproofing material, and the like. Various kinds of monomers and hydrophilic polymers have been proposed as a raw material for the water absorbent resin. In particular, a polyacrylic acid (salt)-based water absorbent resin in which acrylic acid and/or salt thereof are/is used as a monomer(s) is industrially in widespread use because of its high water absorption performance.

Recently, an absorbent article has been required to contain a high-concentration water absorbent resin, and importance has been placed on liquid permeability of water absorption properties. The reason for this is as follows. A water absorbent resin absorbs water-based liquid to swell. Therefore, a state called a so-called gel blocking is caused in which a water absorbent resin which has come into contact with a water-based liquid swells, and the water-based liquid does not reach a water absorbent resin layer which is distant from the water-based liquid. It is necessary to prevent the water absorbent resin layer which cannot exhibit water absorption performance from occurring.

On the other hand, a mere increase in liquid permeability deteriorates ability to absorb water-based liquid. As a result, a liquid leakage phenomenon is caused in which a water-based liquid which has not been absorbed leaks from an absorbent article. Consequently, a water absorbent resin fails to exhibit a sufficient water absorption performance.

A person skilled in the art has advanced development of various additives so as to improve performance of water absorbent resins. For example, Patent Literature 1 discloses coating a water absorbent resin with polyammonium carbonate obtained by adding carbon dioxide to polyamine so as to prevent adhesiveness from being expressed, the adhesiveness being expressed in a case where the water absorbent resin is merely coated with polyamine, so that the water absorbent resin has an excellent gel bed permeability (GBP). Patent Literature 2 discloses adding, to a water absorbent resin, a suspension containing water-insoluble metal phosphate and polyamine and further containing another hydrophobic polymer, and then heating the mixture at 120° C. or higher, so that the water absorbent resin has excellent saline flow conductivity (SFC), free swell rate (FSR) and fixed height absorption (FHA). Patent Literature 3 discloses a water absorbent resin having excellent saline flow conductivity (SFC) and fixed height absorption (FHA), the water absorbent resin being obtained by adding 10 ppm to 1000 ppm of polyamine and a hydrophobic polymer.

Patent Literature 4 discloses a water absorbent resin having excellent Centrifuge Retention Capacity (CRC) and saline flow conductivity (SFC), the water absorbent resin being obtained by adding a modified cationic polymer containing a primary amino group and/or a secondary amino group.

Patent Literature 5 discloses coating, with water, an aqueous solution, alkanolamine, a polymer and/or a wax, to obtain a water absorbent resin excellent in abrasion resistance. Patent Literature 6 discloses coating at least a surface with a polymer and/or a wax to obtain a water absorbent resin excellent in abrasion resistance. Patent Literature 7 discloses a coating technique with a thermoplastic polymer.

Patent Literature 8 discloses a water absorbent resin which is unlikely to come off from cellulose fiber in an absorbent article, the water absorbent resin being obtained by adding a cationic polymer having a mass average molecular weight of not less than 2000 which cationic polymer can react with a carboxyl group to form an ionic bond.

Patent Literatures 9 and 10 disclose a water absorbent polymer in which a particle of the water absorbent polymer has a crosslinked surface to which powder of water-insoluble phosphate (calcium phosphate in Examples) is fixed with dendrimer (polypropylene imine, polyamide amine or polyester amid). Patent Literatures 9 and 10 further disclose that a resultant water absorbent polymer has high SFC, AAP and CRC.

Patent Literatures 11 and 12 (particularly, for example, Examples 1 through 6 of Patent Literature 11) disclose a water absorbent polymer in which a particle of the water absorbent resin has a crosslinked surface to which powder of polyvalent metal salt (aluminum sulfate in Examples) is fixed with a liquid-permeability adjusting agent (such as polyethylene glycol).

Patent Literatures 13 and 14 disclose a water absorbent polymer in which a particle of the water absorbent polymer has a crosslinked surface to which powder of polyvalent metal salt (powder of aluminum sulfate in Examples) is fixed with an organic polymer bonding agent (polyethylene glycol, such as VORANOL 230-238).

Patent Literature 15 discloses a water absorbent polymer in which a particle of the water absorbent polymer has a crosslinked surface to which powder of a polyvalent metal compound (such as silica or alumina) is fixed with polyethylene glycol.

Patent Literatures 16 and 17 disclose a high-absorbent polymer composition containing (i) a water-insoluble inorganic metal compound (preferably, metal phosphate, titanium borate, aluminum borate, iron borate, magnesium borate, manganese borate or calcium borate) and (ii) a polymer coating (preferably, a polymer coating selected from polyolefin, polyethylene, polyester, polyurethane, polyamide, linear low-density polyethylene, ethylene acrylic acid copolymer, styrene copolymer, ethylene alkyl methacrylate copolymer, polypropylene, maleic acid modified polypropylene, ethylene vinyl acetate copolymer, a blend thereof, and a copolymer thereof).

Patent Literature 18 discloses a high water absorbent polymer having a high liquid permeability, the high water absorbent polymer being coated with water-insoluble inorganic powder and a thermoplastic polymer (preferably, a thermoplastic polymer selected from the group consisting of polyolefin, polyethylene, polyester, polyurethane, linear low-density polyethylene (LLDPE), ethylene acrylic acid copolymer (EAA), styrene copolymer, ethylene alkyl methacrylic acid copolymer (EMA), polypropylene (PP), ethylene vinyl acetate copolymer (EVA), a blend thereof, and a copolymer thereof).

Patent Literature 19 discloses a water absorbent material coated with an elastic membrane forming polymer such as polyether polyurethane.

Patent Literatures 22 through 28 disclose a water absorbent polymer whose liquid permeability (such as SFC and/or GBP) has been improved by using an organic or inorganic polyvalent metal salt (such as aluminum lactate or aluminum sulfate) simultaneously with or separately from surface crosslinking.

Patent Literatures 20 and 21 disclose an oxazolin-based polymer and a polyamide polyamine-epihalohydrin adduct, respectively, as a technique of surface crosslinking a water absorbent resin with a polymer crosslinking agent other than the techniques (described in Patent Literatures 1 through 19) of coating a surface of a water absorbent resin with a polymer compound.

On the other hand, these techniques have problems such as (i) insufficient liquid permeability and water absorbing speed of a resultant water absorbent polymer, (ii) causing coloring of a water absorbent resin, and (iii) causing odor to be emitted. It is therefore desirable to further improve these techniques.

As such, in order to improve liquid permeability (such as SFC), various additives have been proposed. Though these additives (particularly, addition of a polymer) improve the liquid permeability, these additives generally deteriorate fixed height absorption (FHA) and water absorbing speed (such as FSR), particularly the FHA. Moreover, a relatively large amount of additive (particularly, a polymer) (for example, in % order) is required to bring about an effect. Accordingly, these additives are disadvantageous in terms of cost and absorption capacity. These conventional techniques further have difficulty attaining both the liquid permeability (such as SFC) and the FHA (and the water absorbing speed).

CITATION LIST

Patent Literature

[Patent Literature 1]
Japanese Translation of PCT International Application, Tokuhyo No. 2008-528751
[Patent Literature 2]
Japanese Translation of PCT International Application, Tokuhyo No. 2010-534751
[Patent Literature 3]
Japanese Translation of PCT International Application, Tokuhyo No. 2010-534752
[Patent Literature 4]
Japanese Translation of PCT International Application, Tokuhyo No. 2010-540206
[Patent Literature 5]
Japanese Translation of PCT International Application, Tokuhyo No. 2010-513632
[Patent Literature 6]
Japanese Translation of PCT International Application, Tokuhyo No. 2010-513631
[Patent Literature 7]
Japanese Translation of PCT International Application, Tokuhyo No. 2010-533766
[Patent Literature 8]
Japanese Patent Application Publication, Tokukaihei, No. 05-031362 (1993)
[Patent Literature 9]
Japanese Translation of PCT International Application, Tokuhyo No. 2007-530752
[Patent Literature 10]
Japanese Translation of PCT International Application, Tokuhyo No. 2007-529292
[Patent Literature 11]
Japanese Translation of PCT International Application, Tokuhyo No. 2006-526691
[Patent Literature 12]
Japanese Translation of PCT International Application, Tokuhyo No. 2006-524541
[Patent Literature 13]
Japanese Translation of PCT International Application, Tokuhyo No. 2001-523289
[Patent Literature 14]
Japanese Translation of PCT International Application, Tokuhyo No. 2009-534483
[Patent Literature 15]
Japanese Patent Application Publication, Tokukai, No. 2005-095759
[Patent Literature 16]
Japanese Translation of PCT International Application, Tokuhyo No. 2010-522255
[Patent Literature 17]
Japanese Translation of PCT International Application, Tokuhyo No. 2010-522008
[Patent Literature 18]
Japanese Translation of PCT International Application, Tokuhyo No. 2007-510045
[Patent Literature 19]
Japanese Translation of PCT International Application, Tokuhyo No. 2008-538121
[Patent Literature 20]
Japanese Patent Application Publication, Tokukai, No. 2000-197818
[Patent Literature 21]
U.S. Pat. No. 4,824,901
[Patent Literature 22]
Pamphlet of International Publication No. WO2012/102406
[Patent Literature 23]
Pamphlet of International Publication No. WO2012/102407
[Patent Literature 24]
Pamphlet of International Publication No. WO2000/053664
[Patent Literature 25]
Pamphlet of International Publication No. WO2000/053644
[Patent Literature 26]
Pamphlet of International Publication No. WO2001/074913
[Patent Literature 27]
Pamphlet of International Publication No. WO2007/121937
[Patent Literature 28]
Pamphlet of International Publication No. WO2008/092843
[Patent Literature 29]
Pamphlet of International Publication No. WO2009/080611
[Patent Literature 30]
Pamphlet of International Publication No. WO2010/108875

SUMMARY OF INVENTION

Technical Problem

An object of the present invention is to provide (i) a water absorbent resin material which attains high liquid permeability (such as SFC), water absorbing speed (such as FSR) and fixed height absorption (FHA), and which does not have problems of coloring and odor and (ii) a method for producing the water absorbent resin material.

Solution to Problem

The inventors of the present invention made a diligent study in order to attain the object, and found that it was possible to attain all of liquid permeability, water absorbing speed and FHA without coloring and odor by adding an extremely small amount of a specific water-soluble or water-dispersible polymer to a surface-crosslinked water absorbent resin that essentially contains a water-soluble polyvalent cation, specifically by using, as a specific polymer, 0.001 mass % to 0.2 mass % of a water-soluble or water-dispersible polymer whose Log P is not less than 1.0. The inventors completed the present invention.

That is, the present invention provides a water absorbent resin material, including:

(A) a water absorbent resin particle having a carboxyl group;

(B) a covalent surface crosslinking agent in which the number of carbons is not more than 10;

(C) 0.001 mass % to 0.2 mass % of a water-soluble or water-dispersible polymer whose Log P defined by Expression 1 is not less than 1.0; and (D) 0.001 mass % to 1 mass % of a water-soluble polyvalent cation, the water absorbent resin material having not less than 20 g/g of a fixed height absorption (FHA) at a height of 20 cm,

[Mathematical Expression 1]

$$\text{Log}P = \sum_{i=1}^{n} (VM\text{Log}P(i) \times MR(i))$$ (Expression 1)

where VM Log P(i) is a calculation value of an "n-octanol/water partition coefficient", at 25° C., of a virtual monomer unit (Virtual Monomer (VM)) in which both ends of a polymer repeating unit (i) are methylated, and MR(i) is a "molar ratio (Mol Ratio (MR))" of the polymer repeating unit (i).

Advantageous Effects of Invention

A water absorbent resin material of the present invention is excellent in liquid permeability, absorption capacity and water absorbing speed, and is less colored. It is therefore possible to produce, with the water absorbent resin material, an excellent hygienic material, such as a diaper, which less leaks liquid and less returns liquid which has been absorbed to be unabsorbed again.

DESCRIPTION OF EMBODIMENTS

The following description will specifically discuss a water absorbent resin material of the present invention, and a method of the present invention for producing the water absorbent resin material. However, the scope of the present invention is not limited to the description. Examples other than examples described below can be appropriately modified and put into practice within the range which does not impair the present invention. In the present invention, "weight" is synonymous with "mass", "wt %" is synonymous with "mass %", and "part by weight" is synonymous with "part by mass". This specification uses only mass, mass %, and part by mass.

[1] Definition of Terms (1-1) "Water Absorbent Resin Material"

The term "water absorbent resin material" in this specification means a water-based liquid gelatinizer obtained by subjecting a water absorbent resin to a surface crosslinking step, and, if necessary, to a step of adding a liquid-permeability improving agent. In addition to the liquid-permeability improving agent, a chelating agent, a reducing agent, an antioxidant, an anti-coloring agent, etc. may be each added to or contained in the water-based liquid gelatinizer by 0 mass % to 10 mass %, and preferably 0.1 mass % to 1 mass %.

(1-2) "Surface-Crosslinked Water Absorbent Resin" and "Water Absorbent Resin Particle"

The term "surface-crosslinked water absorbent resin" in this specification means a water-based liquid gelatinizer obtained by subjecting a water absorbent resin to a surface crosslinking step. A water-based liquid gelatinizer obtained by subjecting a water absorbent resin to the surface crosslinking step after subjecting to a surface crosslinking agent addition step and a liquid permeability improving agent addition step is also called the surface-crosslinked water absorbent resin.

The surface-crosslinked water absorbent resin is sometimes called a water absorbent resin particle or a surface-crosslinked water absorbent resin particle in this specification.

(1-3) "Water Absorbent Resin"

The term "water absorbent resin" in this specification means a water-swelling and water-insoluble polymer gelatinizer. Note that "water-swelling" means that CRC (water absorption capacity without load) defined by ERT441.2-02 is not less than 5 [g/g], and "water-insoluble" means that Extractables (water soluble component, hereinafter abbreviated to "Ext.") defined by ERT470.2-02 is in a rage from 0 mass % to 50 mass %.

The water absorbent resin is not limited to being totally a polymer (100 mass %). As long as the water absorbent resin maintains the performance, the water absorbent resin may contain an additive etc. Even a water absorbent resin composition containing a small amount of additive is generically called the water absorbent resin in the present invention. Note that the water absorbent resin is in the shape of a sheet, fiber, film, gel, powder, or the like. The water absorbent resin is more preferably in the shape of powder. The water absorbent resin is particularly preferably a powdery water absorbent resin having a particle size and a moisture content which are described later.

The term "polyacrylic acid (salt)-based water absorbent resin" in this specification means a polymer (i) which optionally contains a graft component and (ii) whose main component is an acrylic acid and/or a salt thereof (hereinafter referred to as acrylic acid (salt)) as a repeating unit.

More specifically, the "polyacrylic acid (salt)-based water absorbent resin" is a polymer in which acrylic acid (salt) accounts for 50 mol % to 100 mol % in the total monomer content (except a crosslinking agent) to be polymerized, more preferably a water absorbent resin in which acrylic acid (salt) accounts for 70 mol % to 100 mol % in the total monomer content, still more preferably a water absorbent resin in which acrylic acid (salt) accounts for 90 mol % to 100 mol % in the total monomer content, and particularly preferably a water absorbent resin in which acrylic acid (salt) accounts for substantially 100 mol % in the total monomer content. Moreover, in the present invention, a polyacrylate (neutralized) polymer is also generically called "polyacrylic acid (salt)-based water absorbent resin".

(1-4) "EDANA" and "ERT"

The term "EDANA" stands for European Disposables and Nonwovens Associations. The term "ERT" stands for EDANA Recommended Test Methods, which is the European-standard (actually the global-standard) method of measuring water absorbent resins. Note that, in the present invention, unless otherwise specified, physical properties of a water absorbent resin are measured in conformity with a master copy of the ERT (Known Literature: 2002 revised version).

(a) "CRC" (ERT441.2-02)

The term "CRC" stands for Centrifuge Retention Capacity, and means absorption capacity without load (hereinafter may be referred to as "absorption capacity"). Specifically, the "CRC" means absorption capacity (Unit: [g/g]) observed after 0.200 g of water absorbent resin wrapped in unwoven cloth is allowed to freely swell in a large excess of a 0.9 mass % sodium chloride aqueous solution (physiological saline) for 30 minutes and then drained with a centrifugal machine.

(b) "AAP" (ERT442.2-02)

The term "AAP" stands for Absorption Against Pressure, and means absorption capacity under load. Specifically, the "AAP" means absorption capacity (Unit: [g/g]) observed after 0.900 g of water absorbent resin is allowed to swell in a 0.9 mass % sodium chloride aqueous solution (physiological saline) under load of 4.83 kPa (0.7 psi) for 1 hour.

(c) "PSD" (ERT420.2-02)

The term "PSD" stands for Particle Size Distribution, and means a particle size distribution measured by sieve classification. It should be noted that a mass average particle diameter (D50) and a particle diameter distribution range (i.e., a logarithmic standard deviation ($\sigma\zeta$) of a particle size distribution) are measured by the method as set forth in "(3) Mass-average particle diameter (D50) and logarithmic standard deviation ($\sigma\zeta$) of particle diameter distribution" on page 20, lines 11 through 30 of the specification of European Patent EP1594556 B1.

(1-5) "Liquid Permeability"

The degree of flowing of a liquid between particles of a swollen water absorbent resin under load or without load, in other words, a swollen gel is referred to as "liquid permeability". The "liquid permeability" is measured typically as SFC (Saline Flow Conductivity) or GBP (Gel Bed Permeability).

"SFC (Saline Flow Conductivity)" is liquid permeability of 1.5 g of a water absorbent resin for a 0.69 mass % sodium chloride aqueous solution under load of 2.07 kPa, and is measured according to the SFC test method described in the specification of U.S. Pat. No. 5,669,894. Moreover, "GBP" is liquid permeability of a water absorbent resin for a 0.90 mass % sodium chloride aqueous solution wherein the water absorbent resin is under load or allowed to freely swell. "GBP" is measured according to the GBP test method described in the pamphlet of International Publication No. WO2005/016393.

(1-6) "Log P"

"Log P" of the present application indicates n-octanol/water partition coefficient (Log 10Pow), and can be found according to (i) OECD Test Guideline ("C (81) 30/Final Annex 1" adopted by the OECD Council) 107 or (ii) Japanese Industrial Standards Z7260-107 (2000) "Measurement of Partition Coefficient (1-octanol/water)-Shake Flask Method". The present invention basically uses a value calculated by the following calculation method.

As the following values VM Log P(i) and MS Log P(i) employed are values calculated at 25° C. with ACD/Log P DB Releace 100 Product Version 10.01 manufactured by Advanced Chemistry Development. Unless otherwise specified, the Log P is a so-called common logarithm whose base is 10.

First calculated is a Log P (VM Log P (i) where "i" is a serial number starting from 1 so that each monomer is identified) of a virtual monomer unit (Virtual Monomer) in which a methyl group is given to a polymerization reaction site of each monomer (i) where "i" is a serial number starting from 1 so that each monomer is identified.

The virtual monomer unit is based on a repeating structure in a polymer, and is not sometimes identical with a monomer which is actually used to produce a polymer. The virtual monomer unit is specifically determined as below.

In a case where a monomer is a polymerizable unsaturated monomer, a polymerization reaction site is C=C, and two methyl groups are introduced to an unsaturated bond.

In a case where a monomer is a ring-opening polymerizable monomer, two methyl groups are introduced to a ring-opening unit of a ring structure (to an epoxy group, for example, in a case of ethylene oxide).

In a case where a monomer is a condensation-polymerizable monomer, a methyl group is introduced to a condensation polymerization unit (e.g., ester, ether, or amide).

In a case where a monomer has a repeating unit of a cellulose skeleton, a methyl group may be introduced to each polyether unit serving as a condensation polymerization unit. In a case of a polyunsaturated monomer, such as polyalkylene oxide having an unsaturated group (e.g., monoacrylate of methoxypolyethylene glycol), two methyl groups are introduced to an unsaturated bond (e.g., C=C of acrylic acid). Simultaneously with the introduction, a polymer unit in a monomer (e.g., polyethylene oxide) is decomposed, and a methyl group is introduced, and a condensation polymerization unit (e.g., COOH of acrylic acid) is further methylated.

For example, in a case where a polymer obtained by polymerization of an unsaturated monomer is polyethylene, a monomer (1) is ethylene, and a VM Log P(1) is a Log P of n-butane. In a case where the polymer obtained by polymerization of the unsaturated monomer is a styrene-butadiene copolymer, the monomer (1) is styrene, a monomer (2) is butadiene, the VM Log P(1) is a Log P of 2-phenylbutane, and VM Log P(2) is a Log P of 3-hexene. In a case where the polymer obtained by polymerization of the unsaturated monomer is a 100% saponified polyvinyl alcohol, the VM Log P(1) is a Log P of 3-butanol.

In a case where a polymer obtained by polymerization of a ring-opening polymerizable monomer is polyethylene glycol, the monomer (1) is ethylene oxide, and the VM Log P(1) is a Log P of methyl-n-propylether.

In a case where a polymer obtained by polymerization of a condensation-polymerizable monomer is polyaspartic acid, the monomer (2) is aspartic acid, and the VM Log P(1) is a Log P of N-methyl-methylaspartate ester.

Then, the VM Log P(i) is corrected with a molar ratio (Mol Ratio, MR(i) where "i" is a serial number starting from 1 so that each monomer is identified) of each monomer included in a polymer whose Log P is to be calculated (VM Log P(i)×MR(i)). Note that a monomer (j) which is not included in the polymer has an MR(j) of 0. In a case of a homopolymer, the MR(i) is 1.

Lastly, correction values of all monomers are totalized, so that a Log P is calculated (see Expression 1 below).

[Mathematical Expression 2]

$$\text{Log}P = \sum_{i=1}^{n}(V\!M\text{Log}P(i)\times MR(i)) \quad \text{(Expression 1)}$$

(where VM Log P(i) is a calculation value of an n-octanol/water partition coefficient, at 25° C., of a virtual monomer unit (Virtual Monomer) in which a methyl group is given to a polymerization reaction site of each monomer (i) (where "i" is a serial number starting from 1 so that each monomer is identified), and where MR(i) is a molar ratio of each monomer (i)) For example, acrylic acid homopolymer has a Log P of 1.12, and styrene homopolymer has a Log P of 4.09.

(1-7) "Surface Hydrophobic Index"

The Log P is a value indicative of macrostructural hydrophobicity where all polymers to be added are regarded as one, whereas a surface hydrophobic index indicates hydrophobicity of a water absorbent resin surface.

The surface hydrophobic index is specifically calculated as follows. First, Log P(i) of each monomer (i) (a monomer based on a repeating unit determined when the above virtual monomer unit (Virtual Monomer) is calculated, i.e., a monomer having a reaction site to which no methyl group is given) included in a polymer is corrected with the above MR(i), so that MS Log P(i) (Monomer State Log P) is calculated (MS Log P(i)=Log P(i)×MR(i)).

Then, the total of MS Log P(i) of each monomer included in the polymer which is water-soluble or water-dispersible is multiplied by added amount (mass %) of the water-soluble or water-dispersible polymer to be added to a water absorbent resin, so that the surface hydrophobic index is found (see Expression 2 below).

[Mathematical Expression 3]

$$\text{Surface Hydrophobic Index} = \sum_{i=1}^{n}(MS\text{Log}P(i))\times \text{added amount} \\ \text{of the polymer }(C)\times 100 \quad \text{(Expression 2)}$$

(where added amount of polymer (C) is mass % of the polymer (C), relative to a water absorbent resin to which the polymer (C) has not been added)

The surface hydrophobic index indicates how much hydrophobicity of a water absorbent resin particle surface is increased due to the polymer added to the water absorbent resin.

(1-8) Others

In this specification, "X to Y" indicative of a range means "not less than X and not more than Y" which includes both X and Y. The weight unit "t (ton)" means "Metric ton". Unless otherwise specified, "ppm" means "ppm by mass". The wording " . . . acid (salt)" means " . . . acid and/or salt thereof". The wording "(meth)acrylic" means "acrylic and/or methacrylic". Unless otherwise specified, physical properties, etc. are measured at room temperature (23° C.) at a relative humidity of 50% RH.

[2] Method for Producing Water Absorbent Resin Material

The following description will discuss a method for producing a water absorbent resin material of the present invention, by explaining, as an example, a method for producing a water absorbent resin material containing a polyacrylic acid (salt)-based water absorbent resin particle.

(2-1) Step of Preparing Acrylic Acid (Salt)-Based Monomer Aqueous Solution

In this specification, the term "acrylic acid (salt)-based monomer aqueous solution" is an aqueous solution of a monomer(s) whose main component is acrylic acid (salt). The acrylic acid (salt)-based monomer aqueous solution, if necessary, may contain a component constituting a water absorbent resin, such as a crosslinking agent, a graft component, a minute component (a chelating agent, a surfactant, a dispersing agent, or the like), etc. The acrylic acid (salt)-based monomer aqueous solution can be polymerized as it is with a polymerization initiator added thereto.

The acrylic acid (salt) may be unneutralized or may be a salt (fully neutralized or partially neutralized). Moreover, the monomer aqueous solution may exceed its saturating concentration. The acrylic acid (salt)-based monomer aqueous solution of the present invention also encompasses a supersaturated aqueous solution of or a slurry aqueous solution (aqueous dispersion solution) of the acrylic acid (salt). From the viewpoint of physical properties of a resultant water absorbent resin particle and a resultant water absorbent resin material, it is preferable to use an acrylic acid (salt)-based monomer aqueous solution having a concentration of not more than the saturating concentration.

A solvent for the monomer(s), i.e., a solvent used in the acrylic acid (salt)-based monomer aqueous solution is preferably water. In a case where the solvent is water, an acrylic acid (salt)-based monomer is dealt as an aqueous solution. The term "aqueous solution" as used herein is not limited to a case where 100 mass % of the solvent is water. The aqueous solution in the present invention also encompasses an aqueous solution which contains water in combination with 0 mass % to 30 mass % of, preferably 0 mass % to 5 mass % of a water-soluble organic solvent (e.g., alcohol).

In this specification, the term "acrylic acid (salt)-based monomer aqueous solution which is being prepared" refers to an aqueous solution of acrylic acid (salt), which is a monomer aqueous solution whose main component is acrylic acid (salt) to which monomer aqueous solution not all constituent components have been added. Specifically, the "acrylic acid (salt)-based monomer aqueous solution which is being prepared" is an acrylic acid aqueous solution or a fully or partly neutralized acrylic acid salt aqueous solution.

The acrylic acid (salt)-based monomer aqueous solution which is being prepared is further neutralized, mixed with water as a solvent, or mixed with the minute component or the like, thereby being prepared as a fully-prepared acrylic acid (salt)-based monomer aqueous solution. It should be noted that the fully-prepared acrylic acid (salt)-based monomer aqueous solution, when it is in such a state that it has not been introduced into a polymerizer or has been introduced into the polymerizer but whose polymerization has not been started yet, is referred to as "acrylic acid (salt)-based monomer aqueous solution which has been prepared but has not been polymerized".

(Monomer)

The acrylic acid (salt)-based monomer of the present invention is not particularly limited, provided that a water absorbent resin can be produced therefrom through polymerization. Examples of the acrylic acid (salt)-based monomer encompass: anionic unsaturated monomers and salts thereof such as (meth)acrylic acid, (anhydrous)maleic acid, itaconic acid, cinnamic acid, vinylsulfonic acid, allyltoluenesulfonic acid, vinyltoluene sulfonic acid, styrene sulfonic acid, 2-(meth)acrylamide-2-methylpropanesulfonic acid, 2-(meth)acryloyl ethanesulfonic acid, 2-(meth)acryloyl propanesulfonic acid, and 2-hydroxyethyl (meth)acryloyl phosphate; mercapto group-containing unsaturated monomers; phenolic hydroxide group-containing unsaturated monomers; amide group-containing unsaturated monomers such as (meth)acrylamide, N-ethyl (meth)acrylamide, and N,N-dimethyl (meth)acrylamide; amino group-containing unsaturated monomers such as N,N-dimethylamino ethyl (meth)acrylate, N,N-dimethylaminopropyl (meth)acrylate, and N,N-dimethylaminopropyl (meth)acrylamide; and like monomers.

The content (used amount) of the acrylic acid (salt)-based monomer is normally not less than 50 mol %, preferably not less than 70 mol %, more preferably not less than 80 mol %, still more preferably not less than 90 mol %, and particularly preferably not less than 95 mol % (upper limit is 100 mol %), relative to a total monomer content (excluding an internal crosslinking agent). It should be noted that the polyacrylic acid (salt) in the present invention is not limited to an unneutralized one (neutralization ratio: 0 mol %) but may be partially neutralized or fully neutralized (neutralization ratio: 100 mol %).

In the present invention, a neutralization ratio of the acrylic acid (salt)-based monomer or a polymerized water-containing gel-like crosslinked polymer is not particularly limited, but is preferably in a range from 40 mol % to 90 mol %, more preferably in a range from 50 mol % to 80 mol %, and still more preferably in a range from 60 mol % to 74 mol %, from the viewpoint of (i) physical properties of a resultant water absorbent resin particle and (ii) reactivity of a surface crosslinking agent with a water absorbent resin.

It is preferable that the neutralization ratio be within the above range. This is because a low neutralization ratio tends to lower water absorbing speed (for example, FSR), and a high neutralization ratio tends to lower reactivity of the polyacrylic acid (salt)-based water absorbent resin with a surface crosslinking agent, particularly with a dehydration reactive surface crosslinking agent (later described), still particularly with alkylene carbonate, thereby resulting in low productivity, low liquid permeability (for example, SFC), and/or low absorption capacity under load (for example, AAP). Note that, in a case where the water absorbent resin is applied to absorbent articles, such as disposable diapers, which possibly come into contact with human body, neutralization after polymerization is not required.

The acrylic acid (salt)-based monomer or the water-containing gel-like crosslinked polymer may be partly or totally a salt, from the viewpoint of absorption capacity without load (CRC) and absorption capacity under load (AAP) of a water absorbent resin material obtained as a final product. The acrylic acid (salt)-based monomer or the water-containing gel-like crosslinked polymer is preferably a monovalent salt such as sodium salt, lithium salt, potassium salt, ammonium salt, or amines. Among them, the acrylic acid (salt)-based monomer or the water-containing gel-like crosslinked polymer is more preferably alkaline metal salt, still more preferably sodium salt and/or potassium salt, and particularly preferably sodium salt from the viewpoint of cost and physical properties.

(Polymerization Inhibitor)

The acrylic acid (salt)-based monomer of the present invention contains a polymerization inhibitor. Although the polymerization inhibitor is not particularly limited, examples of the polymerization inhibitor encompass N-oxyl compounds, manganese compounds, substituted phenol compounds, and the like, which are disclosed in International Publication No. WO2008/096713. Among these compounds, the substituted phenol compounds are more preferable, and among the substituted phenol compounds, methoxy phenols are particularly preferable.

Examples of the methoxy phenols encompass o, m, p-methoxy phenol, methoxy phenols having one or more substituents such as a methyl group, a t-butyl group, or a hydroxyl group, and the like. In the present invention, p-methoxy phenol is particularly preferable.

The polymerization inhibitor content in the acrylic acid (salt)-based monomer is preferably in a range from 5 ppm to 200 ppm, more preferably in a range from 5 ppm to 160 ppm, 10 ppm to 160 ppm, 10 ppm to 100 ppm, and 10 ppm to 80 ppm, in this order, and most preferably in a range from 10 ppm to 70 ppm. The polymerization inhibitor content of not more than 200 ppm is preferable because deterioration in color tone (coloring, i.e., yellowing or change into yellow) less occurs on a resultant water absorbent resin material. The polymerization inhibitor content of not less than 5 ppm, that is, a case where the polymerization inhibitor is not removed by purification such as distillation, is preferable because unintentional polymerization is unlikely to take place.

(Internal Crosslinking Agent)

In the present invention, polymerization is carried out, if necessary, with an internal crosslinking agent. A publicly-known internal crosslinking agent is used as the internal crosslinking agent. Examples of the internal crosslinking agent encompass: N,N'-methylene bis(meth)acrylamide, (poly)ethylene glycol di(meth)acrylate, (poly)propyleneglycol di(meth)acrylate, trimethylolpropane tri(meth)acrylate, glycerine tri(meth)acrylate, glycerine acrylate methacrylate, ethyleneoxide modified trimethylol propane tri(meth)acrylate, pentaerythritol hexa(meth)acrylate, triallyl cyanurate, triallyl isocyanurate, triallyl phosphate, triallylamine, poly(meth)allyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth)acrylate, and the like. In consideration of reactivity, one or more kinds of compounds among them can be used. Especially, it is preferable to use a compound having two or more polymerizable unsaturated groups.

In a case where two or more kinds of internal crosslinking agents are used in combination, an internal crosslinking structure can be changed by changing reactivities of functional groups of the internal crosslinking agents. Therefore, in this case, it is preferable to (i) select, from the above-described compounds such as an amide compound, a (meth)acrylate compound, an allylic compound, an amine compound, an imine compound, an alcohol compound, a carbonate compound, and a glycidyl compound, internal crosslinking agents different in functional group and (ii) use the internal crosslinking agents in combination.

A used amount of the internal crosslinking agent can be determined as appropriate, depending on desired physical properties of the water absorbent resin material. However, the used amount of the internal crosslinking agent is preferably in a range from 0.001 mol % to 5 mol %, more preferably in a range from 0.005 mol % to 2 mol %, and still more preferably in a range from 0.01 mol % to 1 mol %, relative to a total amount of the acrylic acid (salt)-based monomer. In a case where two or more kinds of internal crosslinking agents are used in combination, the used amount of each of the internal crosslinking agents is preferably in a range from 0.001 mol % to 5 mol %, more preferably in a range from 0.005 mol % to 2 mol %, and still more preferably in a range from 0.01 mol % to 1 mol %, relative to the total amount of the acrylic acid (salt)-based monomer.

In a case where the used amount of the internal crosslinking agent (or a total amount of the two or more kinds of internal crosslinking agents used in combination) is not less than 0.001 mol %, a water soluble component of the resultant water absorbent resin material becomes small, and a sufficient amount of water can be absorbed under load. Furthermore, in a case where the used amount of the internal crosslinking agent is not more than 5 mol %, the resultant water absorbent resin material does not increase its crosslinking density too much, and can absorb a sufficient amount of water. It should be noted that the internal crosslinking agent(s) may be added in whole to the acrylic acid (salt)-based monomer aqueous solution which has been prepared but has not been polymerized, or part of the internal crosslinking agent(s) may be added after polymerization starts.

(Dispersing Agent)

A dispersing agent usable in the present invention is not particularly limited, but is preferably a water absorbent polymer dispersing agent or a water absorbable hydrophilic polymer dispersing agent, and more preferably a water-soluble polymer dispersing agent. A mass average molecular weight of the dispersing agent is determined as appropriate depending on kinds of dispersing agent. However, the weight average molecular weight of the dispersing agent is preferably in a range from 500 to Ser. No. 10/000,000, more preferably in a range from 5,000 to 5,000,000, and particularly preferably in a range from 10,000 to 3,000,000.

The dispersing agent is not limited to a specific kind of dispersing agent. Examples of the dispersing agent encompass hydrophilic polymers such as starch, starch derivative, cellulose, cellulose derivative, polyvinyl alcohol (PVA), carboxymethyl cellulose (sodium), hydroxyethyl cellulose, polyacrylic acid (salt), and crosslinked polyacrylic acid (salt). Among them, a water-soluble polymer dispersing agent selected from starch, cellulose, and PVA is preferable from the viewpoint of the effect of the present invention.

A used amount of the dispersing agent is preferably more than 0 part by mass and not more than 50 parts by mass, more preferably in a range from 0.01 part by mass to 20 parts by mass, still more preferably in a range from 0.05 part by mass to 10 parts by mass, and particularly preferably in a range from 0.1 part by mass to 5 parts by mass, relative to 100 parts by mass of the acrylic acid (salt)-based monomer.

(2-2) Polymerization Step (Polymerization Method)

Examples of a polymerization method for obtaining the water absorbent resin of the present invention encompass spraying polymerization, droplet polymerization, bulk polymerization, precipitation polymerization, aqueous solution polymerization, reverse phase suspension polymerization, and other polymerizations. In order to attain the object of the present invention, it is more preferable to employ aqueous solution polymerization or reverse phase suspension polymerization, each of which is carried out with an aqueous solution of monomers, and it is still more preferable to employ the aqueous solution polymerization which is carried out with the aqueous solution of monomer.

The aqueous solution polymerization is a method of polymerizing a monomer in a monomer aqueous solution without using a dispersion solvent. This is disclosed in, for example, U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808, European Patent No. 0811636, European Patent No. 0955086, European Patent No. 0922717, and the like.

The reverse phase suspension polymerization is a method of suspending a monomer aqueous solution in a hydrophobic organic solvent and polymerizing a monomer. This is disclosed in, for example, U.S. Pat. No. 4,093,776, U.S. Pat. No. 4,367,323, U.S. Pat. No. 4,446,261, U.S. Pat. No. 4,683,274, U.S. Pat. No. 5,244,735, and the like. Monomers, polymerization initiators, etc. disclosed in these patent literatures are applicable to the present invention.

A concentration of the monomer aqueous solution during the polymerization is not particularly limited, but is preferably in a range from 20 mass % to not more than the saturating concentration, more preferably in a range from 25 mass % to 80 mass %, and still more preferably in a range from 30 mass % to 70 mass %. The concentration of not less than 20 mass % is preferable because productivity increases. It should be noted that polymerization with a monomer slurry (aqueous dispersion solution of acrylate) causes deterioration in physical properties. It is therefore more preferable to carry out the polymerization at not more than the saturating concentration (see Japanese Patent Application Publication, Tokukaihei, No. 1-318021 (1989)).

In order to promote the polymerization and to improve the physical properties, a step of removing dissolved oxygen (for example, a step of substituting the dissolved oxygen with inert gas) may be provided as appropriate during the polymerization. In addition, for the purpose of increasing water absorbing speed, surface area, drying speed, or the like, the monomer aqueous solution may contain air bubbles (particularly inert gas) or various foaming agents (for example, organic or inorganic carbonate, an azo compound, or a urea compound) during the polymerization, and may be foamed so that a resultant polymer has, for example, a volume 1.001 to 10 times as large as that of the monomer aqueous solution during the polymerization or during drying.

The polymerization step in the present invention can be carried out under any of normal atmospheric pressure, reduced pressure, and increased pressure. Preferably, the polymerization step is carried out under normal atmospheric pressure (or under an atmospheric pressure close to the normal atmospheric pressure, typically the normal atmospheric pressure±10 mmHg). Though depending upon kinds of polymerization initiator to be used, temperature at which the polymerization starts is preferably in a range from 15° C. to 130° C., and more preferably in a range from 20° C. to 120° C.

(Polymerization Initiator)

A polymerization initiator used in the present invention is selected as appropriate depending on a polymerization scheme, and is not particularly limited. Examples of the polymerization initiator include photodegradable polymerization initiators, pyrolytic polymerization initiators, redox polymerization initiators, and the like. With any of these polymerization initiators, polymerization of the present invention is initiated.

Examples of the photodegradable polymerization initiators encompass benzoin derivatives, benzyl derivatives, acetophenone derivatives, benzophenone derivatives, azo compounds, and the like.

Examples of the pyrolytic polymerization initiators encompass: persulfates such as sodium persulfate, potassium persulfate, and ammonium persulfate; peroxides such as hydrogen peroxide, t-butyl peroxide, and methyl-ethyl-ketone peroxide; azo compounds such as 2,2'-azobis(2-amidinopropane)dihydrochloride, and 2,2'-azobis[2-(2-imidazoline-2-yl)propane]dihydrochloride; and the like.

Examples of the redox polymerization initiators encompass systems each of which is a combination of (i) a reducing compound such as L-ascorbic acid or sodium hydrogen sulfite with (ii) the foregoing persulfate or peroxide.

Further, it is a preferable aspect to use the photodegradable polymerization initiator and the pyrolytic polymerization initiator in combination. Still further, an active energy ray such as an ultraviolet ray, an electron ray, or a gamma ray may be used alone or used in combination with the polymerization initiator.

A used amount of the polymerization initiator is preferably in a range from 0.0001 mol % to 1 mol %, and more preferably 0.0005 mol % to 0.5 mol %, relative to the total monomer content. The used amount of not more than 1 mol % is preferable because no deterioration in color tone occurs on the water absorbent resin. The used amount of not less than 0.0001 mol % is also preferable because residual monomers are unlikely to increase.

(More Preferable Polymerization Method)

In the present invention, at least one of reverse phase suspension polymerization, spraying polymerization, droplet polymerization, and aqueous solution polymerization, particularly aqueous solution polymerization, is employed as a polymerization method using an acrylic acid (salt)-based monomer aqueous solution, from the viewpoint of (i) physical properties (for example, water absorbing speed and liquid permeability) of a water absorbent resin particle, (ii) polymerization controllability during production of a water absorbent resin, etc.

Examples of a preferable aspect of the aqueous solution polymerization encompass high-temperature starting aqueous solution polymerization, high-concentration aqueous solution polymerization, and high-concentration high-temperature starting aqueous solution polymerization. The high-temperature starting aqueous solution polymerization is such that a polymerization starting temperature is preferably not lower than 40° C., more preferably not lower than 50° C., still more preferably not lower than 60° C., particularly preferably not lower than 70° C., and most preferably not lower than 80° C. (upper limit is a boiling point). The high-concentration aqueous solution polymerization is such that a monomer concentration is preferably not less than 30 mass %, more preferably not less than 35 mass %, still more preferably not less than 40 mass %, and particularly preferably not less than 45 mass % (upper limit is not more than 90 mass %, preferably not more than 80 mass %, and more preferably not more than 70 mass %). The high-concentration high-temperature starting aqueous solution polymerization is a combination of the high-temperature starting aqueous solution polymerization and the high-concentration aqueous solution polymerization.

As a polymerization scheme preferably employed is kneader polymerization or belt polymerization. Examples of a preferable scheme of the aqueous solution polymerization encompass continuous belt polymerization (disclosed in U.S. Pat. No. 4,893,999, U.S. Pat. No. 6,241,928, U.S. Patent Application Publication No. 2005/215734, Pamphlet of International Publication No. WO2008/114847, etc.), continuous kneader polymerization, batch kneader polymerization (disclosed in U.S. Pat. No. 6,987,151, U.S. Pat. No. 6,710,141, Pamphlet of International Publication No. WO2008/114848, etc.), and the like.

Further, examples of a combination of the preferable aspect and the preferable polymerization scheme include high-temperature starting continuous aqueous solution polymerization, high-concentration continuous aqueous solution polymerization, and high-concentration high-temperature starting continuous aqueous solution polymerization.

Other preferable examples include batch kneader polymerization and continuous kneader polymerization in each of which (i) polymerization starting temperature is not lower than 15° C. and (ii) monomer concentration is not lower than 30 mass %.

A polymerization starting time of the polymerization (a time period from addition of the polymerization initiator to initiation of the polymerization) is preferably more than 0 second and not more than 300 seconds, and more preferably in a range from 1 second to 240 seconds.

By employing the aforementioned aqueous solution polymerization, it is possible to produce a water absorbent resin with high productivity. It should be noted that the above polymerization methods are preferably applied to an apparatus which produces the water absorbent resin in huge scale, i.e., in a large production volume per line. The production volume is preferably not less than 0.5 [t/hr], more preferably not less than 1 [t/hr], still more preferably not less than 5 [t/hr], and particularly preferably not less than 10 [t/hr].

(2-3) Gel-Crushing Step

This step is an optional step of gel-crushing a water-containing gel-like crosslinked polymer (hereinafter referred to as "hydrogel") obtained through the polymerization step, etc. (particularly, the aqueous solution polymerization) to obtain a hydrogel having a particulate shape (hereinafter referred to as "particulate hydrogel").

The hydrogel obtained through the aqueous solution polymerization is gel-crushed especially by mixing and kneading so as to be grain-refined, so that (i) both water absorbing speed and liquid permeability are attained and (ii) impact resistance is improved. That is, in order to attain the object of the present invention, it is more preferable to adopt the aqueous solution polymerization rather than the reverse phase suspension polymerization which does not require the gel-crushing. It is particularly preferable to adopt aqueous solution polymerization in which gel-crushing is carried out during polymerization (for example, kneader polymerization) or after polymerization (for example, belt polymerization, and further kneader polymerization, if necessary).

A gel-crushing device applicable to the present invention is not particularly limited but is, for example, (i) a batch-type or continuous gel crusher having a plurality of rotational stirring blades such as a double-armed kneader, (ii) a single- or twin-screwed extruder, (iii) a meat chopper, etc. Among them, a screwed extruder having a porous plate at an end is more preferable. An example of the screwed extruder having a porous plate at an end is a screwed extruder disclosed in Japanese Patent Application Publication, Tokukai, No. 2000-063527.

In the gel-crushing step of the present invention, a temperature of the hydrogel (gel temperature) before gel-crushing is preferably in a range from 60° C. to 120° C., and more preferably in a range from 65° C. to 110° C., from the viewpoint of particle size control and physical properties. The gel temperature of not lower than 60° C. does not increase hardness due to properties of the hydrogel. It is therefore easy to control particle shape and particle size distribution in the gel-crushing step. Moreover, the gel temperature of not higher than 120° C. does not increase softness of the hydrogel. It is therefore easy to control the particle shape and the particle size distribution. It should be noted that the gel temperature can be controlled by controlling a temperature during polymerization, heating or cooling after polymerization, etc.

A mass average particle diameter (D50) (defined by sieve classification) of a particulate hydrogel after gel-crushing is preferably in a range from 0.5 mm to 3 mm, more preferably in a range from 0.6 mm to 2 mm, and still more preferably in a range from 0.8 mm to 1.5 mm. A proportion of a coarse particulate hydrogel of not less than 5 mm in particle diameter to a total amount of the particulate hydrogel is preferably in a range from 0 mass % to 10 mass %, more preferably in a range from 0 mass % to 5 mass %, and still more preferably in a range from 0 mass % to 1 mass %.

In the present invention, the polymerization step and gel-crushing step can be carried out by any of the following methods: a kneader polymerization method in which a water-containing gel-like crosslinked polymer is gel-crushed during polymerization; and a method of subjecting, to the gel-crushing step, a water-containing gel-like crosslinked polymer obtained through continuous belt polymerization.

(2-4) Drying Step

This step is a step of drying a hydrogel obtained through the polymerization step, etc. to obtain a dried polymer. In a case where the aqueous solution polymerization is carried out in the polymerization step, a hydrogel is gel-crushed (grain-refined) before and/or after being dried. The dried polymer (aggregates) obtained through the drying step may be supplied directly to a pulverization step.

A drying method employed in the present invention is not particularly limited. Various methods can be employed as the drying method. Specific examples of the drying method include drying by heating, hot-air drying, drying under reduced pressure, infrared drying, microwave drying, azeotropic dehydration drying with a hydrophobic organic solvent, high-humidity drying with use of high-temperature vapor, etc. These drying methods can be used solely, or two of these drying methods can be used in combination. A drying temperature is preferably in a range from 100° C. to 300° C., and more preferably in a range from 150° C. to 250° C.

A drying time is not particularly limited because it depends on a surface area of and a moisture content of the hydrogel, kinds of drying apparatus, and the like. For example, the drying time is preferably in a range from 1 minute to 5 hours, and more preferably in a range from 5 minutes to 1 hour. A resin solid content is preferably not less than 80 mass %, more preferably in a range from 85 mass % to 99 mass %, and still more preferably in a range from 90 mass % to 98 mass %, the resin solid content being calculated from drying loss (drying loss found when 1 g of powder or particles is dried at 180° C. for 3 hours).

(2-5) Pulverization/Classification Step

This step is a step of pulverizing and/or classifying a dried polymer obtained in the drying step to preferably obtain a water absorbent resin having a specific particle size. It should be noted that this pulverization/classification step is different from the above (2-3) Gel-crushing step in that a target to be pulverized has undergone the drying step. A water absorbent resin obtained after the pulverization step may be referred to as a "pulverized water absorbent resin".

(Particle Size Distribution)

A mass average particle diameter (D50) of a water absorbent resin before being surface-crosslinked is preferably in a range from 200 µm to 600 µm, more preferably in a range from 200 µm to 550 µm, still more preferably in a range from 250 µm to 500 µm, and particularly preferably in a range from 350 µm to 450 µm, from the viewpoint of water absorbing speed, liquid permeability, absorption capacity under load, etc. Further, the fewer fine particles having a particle diameter of less than 150 µm defined by standard sieve classification are contained, the better it is. The fine particle content is preferably in a range from 0 mass % to 5 mass %, more preferably in a range from 0 mass % to 3 mass %, and still more preferably in a range from 0 mass % to 1 mass %, from the viewpoint of liquid permeability, etc.

Still further, the fewer coarse particles having a particle diameter of not less than 850 µm, and preferably not less than 710 µm defined by standard sieve classification are contained, the better it is. The coarse particle content is preferably in a range from 0 mass % to 5 mass %, more preferably in a range from 0 mass % to 3 mass %, and still more preferably in a range from 0 mass % to 1 mass %, from the viewpoint of water absorbing speed, etc. Yet further, a water absorbent resin having a particle diameter distribution range of preferably not less than 150 µm and less than 850 µm, and more preferably not less than 150 µm and less than 710 µm is contained by preferably not less than 95 mass %, more preferably not less than 98 mass %, and still more preferably not less than 99 mass % (upper limit is 100 mass %), from the viewpoint of water absorbing speed, liquid permeability, absorption capacity under load, etc.

The particle diameter can be controlled in the polymerization step, the gel-crushing step, or the pulverization/classification step after the drying step. The particle diameter is particularly preferably controlled in the classification step after the drying step. The particle diameter is measured with use of a JIS standard sieve (Z8801-1 (2000)) in conformity with the method defined in International Publication No. WO2004/69915 or EDANA-ERT420.2-02.

The water absorbent resin of the present invention may be in the form of a sphere, in the form of aggregates of the sphere, or in a pulverized non-uniformly shape obtained by subjecting a hydrogel or a dried polymer to the pulverization step. However, from the viewpoint of water absorbing speed, the pulverized non-uniformly shape or a granulated pulverized non-uniformly shaped particle is more preferable.

In order to more suitably attain the object of the present invention, the particle diameter is applied preferably to a particle diameter after surface crosslinking, and further preferably to a water absorbent resin material which is a final product.

(2-6) Fine Powder Recycling Step

The production method of the present invention preferably includes, after the drying step, the classification step (including the second classification step carried out after the surface crosslinking step; hereinafter the same applies to descriptions below) of separating a water absorbent resin fine particle passing through a standard sieve having a mesh size of 150 µm, after which the water absorbent resin fine particle or a mixture thereof with water is recycled (reused) in the steps which are carried out before the drying step. It should be noted that coarse particles removed in the classification step may be re-pulverized if necessary. Moreover, fine particles removed in the classification step may be discarded, used for another purpose, or supplied to this fine powder recycling step.

Removing the fine particles makes it possible to improve liquid permeability (for example, SFC). Moreover, this fine powder recycling step makes it possible to further improve water absorbing speed (for example, FSR).

That is, in the production method of the present invention, the fine powder recycling step refers to a step of (i) separating water absorbent resin fine particles (containing, in particular, not less than 70 mass % of particles having a particle diameter of not more than 150 μm; hereinafter also referred to as "fine powder") which are generated in the drying step, and if necessary, in the pulverization/classification step and (ii) recycling the water absorbent resin fine particles as they are or recycling the absorbent resin fine particles in a hydrated or granulated form before the drying step, preferably in the polymerization step, the gel-crushing step or the drying step.

The fine powder recycling step of recycling the fine powder makes it possible to control particle sizes of a water absorbent resin, a water absorbent resin particle and a water absorbent resin material, and to further improve water absorbing speed.

The fine powder to be recycled may be (i) fine powder of a water absorbent resin which has not been surface-crosslinked or (ii) fine powder of surface-crosslinked water absorbent resin particles. The amount of the recycled fine powder is preferably in a range from 1 mass % to 40 mass %, and more preferably in a range from 5 mass % to 30 mass %, relative to the total mass of a dried polymer.

A fine powder recycling method suitable to the present invention is a method of mixing, with a monomer aqueous solution which has not been polymerized or a hydrogel which is being polymerized, a hydrated or granulated fine powder of a water absorbent resin or a water absorbent resin fine particle, if necessary, with an inorganic fine particle, etc. Note that (i) International Publications Nos. 92/001008 and 92/020723 disclose a method of recycling fine powder into the monomer aqueous solution which has not been polymerized, (ii) International Publications Nos. 2007/074167, 2009/109563, 2009/153196, and 2010/006937 disclose a method of recycling fine powder into the hydrogel which is being polymerized, (iii) U.S. Pat. No. 6,228,930 etc. discloses a method of recycling fine powder into the drying step (into a drying machine). These fine powder recycling methods are preferably employed.

(2-7) Surface Crosslinking Agent Addition Step

This step is a step of preparing a water absorbent resin containing a surface crosslinking agent to be used in the surface crosslinking step. Typically, surface crosslinking is carried out, for example, (i) by adding an organic surface crosslinking agent (later described), then carrying out a heat treatment, (ii) by polymerizing a monomer on a surface of a water absorbent resin, or (iii) by adding a radical polymerization initiator such as persulfate, and then carrying out heating or ultraviolet irradiation. In present invention, it is preferable to add the organic surface crosslinking agent to a water absorbent resin obtained in the classification step, or to a water absorbent resin obtained through the production method of the present invention further including the fine powder recycling step.

The surface crosslinking agent addition step may be carried out simultaneously with a liquid permeability improving agent addition step (later described). Note here that the organic surface crosslinking agent covalently binds to a functional group of, particularly a carboxyl group of a water absorbent resin, and further preferably forms a covalent binding due to dehydration reaction. As the organic surface crosslinking agent used are a polymer organic crosslinking agent or a non-polymer organic crosslinking agent, more preferably a non-polymer organic surface crosslinking agent, still more preferably a non-polymer organic crosslinking agent whose molecular weight is in a range from 60 to 1000, and preferably a water-soluble organic crosslinking agent (an organic crosslinking agent which dissolves in 100 g of water at 25° C. by preferably 1 g or more, still more preferably 5 g or more, and particularly preferably 10 g or more). Note here that low-molecular-weight polyethylene glycols whose mass average molecular weight is not more than 1000 (such as diethylene glycol, triethylene glycol, tetraethylene glycol, pentaethylene glycol, etc.) are classified into a non-polymer organic crosslinking agent. It is also preferable that a surface crosslinking agent used in the present invention be a covalent surface crosslinking agent in which the number of carbons is not more than 10.

(Organic Surface Crosslinking Agent)

Examples of the organic surface crosslinking agent usable in the present invention encompass polyhydric alcohol compounds, epoxy compounds, polyamine compounds, condensates of a polyamine compound and a haloepoxy compound, oxazoline compounds, (mono)oxazolidinone compounds, (di)oxazolidinone compounds, (poly)oxazolidinone compounds, oxetane compounds, alkylene carbonate compounds, and the like, from the viewpoint of physical properties of a resultant water absorbent resin particle or water absorbent resin material. Among them, it is particularly preferable to use a dehydration reactive crosslinking agent including any of a polyhydric alcohol compound, an alkylene carbonate compound, an oxazolidinone compound, and the like, the dehydration reactive crosslinking agent requiring high-temperature dehydration reaction.

The dehydration reactive surface crosslinking agent is a surface crosslinking agent (i) causing dehydration esterification reaction of a carboxyl group, which is a functional group of a polyacrylic acid (salt)-based water absorbent resin, with a hydroxyl group that is a functional group of the surface crosslinking agent, or (ii) causing dehydration amidation reaction of the carboxyl group with an amino group that is a functional group of the surface crosslinking agent. The dehydration reactive surface crosslinking agent further includes cyclic surface crosslinking agents, like the alkylene carbonate compounds and the oxazolidinone compounds, with which a hydroxyl group and an amino group are generated in the process of the reaction.

Though polymer polyamine and non-polymer polyamine are each a dehydration reactive crosslinking agent derived from an amino group, an amino group in a polyamine polymer typically requires an excessively high reaction temperature for dehydration reaction, and is likely to be deteriorated and colored due to high-temperature heating. Therefore, the polyamine polymer is classified into an ionic reaction crosslinking agent or a liquid permeability improving agent at a typically used temperature. The polyamine polymer is used as the ionic reaction crosslinking agent or the liquid permeability improving agent. A polyamine polymer to which an epoxy group has been introduced (modified with epoxy, particularly with glycidyl) is a low-temperature reactive organic surface crosslinking agent.

Specific examples of the organic surface crosslinking agent encompass: polyhydric alcohol compounds such as (di)ethylene glycol, (tri)ethylene glycol, (tetra)ethylene glycol, (poly)ethylene glycol, (di)propylene glycol, (poly)propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, diethanolamine, triethanolamine, pentaerythritol, and sorbitol; epoxy compounds such as (poly)ethylene glycol diglycidyl ether, (di)glycerol polyglycidyl ether, (poly) glycerol polyglycidyl ether, and glycidol; oxazoline compounds such as 2-oxazolidone, N-hydroxyethyl-2-oxazolidone, and 1,2-ethylene bisoxazoline; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; haloepoxy compounds such as epichlorohydrin, epibromohydrin and α-methylepichlorohydrin, and polyamine adducts thereof (for example, epoxy modified polyamine polymer); silane coupling agents such as γ-glycidoxypropyltrimethoxysilane and γ-aminopropyltriethoxysilane; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyloxetane, 3-chloromethyl-3-ethyloxetane, and polyoxetane compounds; cyclic urea compounds such as 2-imidazolidinone; and the like.

Among these, the organic surface crosslinking agent is preferably selected from the polyhydric alcohol compounds, the epoxy compounds, the oxazoline compounds, and the alkylene carbonate compounds. More preferably, the organic surface crosslinking agent is a combination of any compound selected from the polyhydric alcohol compounds and any compound selected from organic surface crosslinking agents (the epoxy compounds, oxazolinone compounds, and the alkylene carbonate compounds) other than polyhydric alcohols.

From the viewpoint of higher physical properties, it is particularly preferable that the organic surface crosslinking agent be a combination of a polyhydric alcohol and a compound (preferably, an epoxy compound or alkylene carbonate, and particularly preferably alkylene carbonate) other than the polyhydric alcohols. Examples of a suitable surface crosslinking method include the methods described in International Publications Nos. WO2012/102406 and WO2012/102407.

The organic surface crosslinking agent is preferably a combination of a plurality compounds selected from the polyhydric alcohols, the alkylene carbonates, the oxazolidinone compounds, the oxetane compounds, and amino alcohol compounds, more preferably a combination of particularly the polyhydric alcohols with cyclic compounds selected from the alkylene carbonates, the oxazolidinone compounds, and the oxetane compounds, and still more preferably a combination of the polyhydric alcohols and the alkylene carbonates.

The polyhydric alcohols are C2-C8 polyhydric alcohols, preferably C3-C6 polyhydric alcohols, and particularly preferably C3 or C4 polyhydric alcohols. Specifically, the polyhydric alcohols are more preferably, for example, diols. Examples of the diols encompass ethylene glycol, propylene glycol, 1,3-propanediol, and 1,4-butanediol.

In a case where plural kinds of dehydration reactive surface crosslinking agents are used in combination, particularly in a case where the dehydration reactive surface crosslinking agent is a combination of any of the polyhydric alcohols and any surface crosslinking agent other than the polyhydric alcohols (particularly a cyclic compound such as alkylene carbonate), a ratio (weight ratio) of any of the polyhydric alcohols to any surface crosslinking agent other than the polyhydric alcohols is typically 1:9 to 9:1, preferably 2:8 to 8:2, more preferably 3:7 to 7:3, and particularly preferably 5:5 to 7:3. At this ratio, any of the polyhydric alcohols and the cyclic compound are used in combination, and still more preferably, any of the polyhydric alcohols (still more preferably C3 to C6 polyhydric alcohol) and alkylene carbonate (still more preferably ethylene carbonate) are used in combination.

The polyhydric alcohol compound suitably used in the present invention is propylene glycol, 1,3-propanediol, or 1,4-butanediol. The epoxy compound suitably used in the present invention is a polyglycidyl compound. The oxazoline compound suitably used in the present invention is 2-oxazolidinone. The alkylene carbonate compound suitably used in the present invention is 1,3-dioxolane-2-one.

A temperature of a solvent where these surface crosslinking agents are mixed with each other is appropriately determined. A too low temperature may result in deterioration in solubility and increase in viscosity. Especially, in a case where a solid non-polymer organic compound (later described) is used as the surface crosslinking agent, particularly, in a case where ethylene carbonate is used as the surface crosslinking agent, it is preferable that the solvent as used is water warmed to room temperature or higher (preferably in a range from 30° C. to 100° C., more preferably in a range from 35° C. to 70° C., and still more preferably in a range from 40° C. to 65° C.).

That is, a compound to be mixed with a non-polymer organic compound (particularly, a solid surface crosslinking agent, further particularly a solid polyhydric alcohol, or a cyclic compound such as alkylene carbonate) is preferably warmed water, and more preferably in the aforementioned temperature range.

The alkylene carbonate compound or the polyhydric alcohol compound, particularly a solid alkylene carbonate compound, is preferably heated in advance before being mixed with water. A heating temperature is preferably higher than a temperature of a surface crosslinking agent solution to which water has been added, i.e., a temperature of a surface crosslinking agent aqueous solution. Specifically, in a case where the solid alkylene carbonate compound is used, it is preferable that polyhydric alcohol, particularly solid polyhydric alcohol be also heated and melted at a temperature preferably in a range from 30° C. to 100° C., more preferably in a range from 35° C. to 70° C., and still more preferably in a range from 40° C. to 65° C.

(Solvent and Concentration)

In a case where the organic surface crosslinking agent is used, a total added amount of the organic surface crosslinking agent is preferably in a range from 0.001 part by mass to 15 parts by mass, and more preferably in a range from 0.01 part by mass to 5 parts by mass, relative to 100 parts by mass of the water absorbent resin to which the organic surface crosslinking agent has not been added.

In a case where a polyhydric alcohol compound and a compound other than polyhydric alcohol are used in combination as the organic surface crosslinking agent, a total added amount of the polyhydric alcohol compound is preferably in a range from 0.001 part by mass to 10 parts by mass, and more preferably in a range from 0.01 part by mass to 5 parts by mass, relative to 100 parts by mass of the water absorbent resin to which the organic surface crosslinking agent has not been added. Furthermore, a total added amount of the compound other than polyhydric alcohol is preferably in a range from 0.001 part by mass to 10 parts by mass, and more preferably in a range from 0.01 part by mass to 5 parts by mass, relative to 100 parts by mass of the water absorbent resin to which the organic surface crosslinking agent has not been added.

A surface crosslinking agent solution preferably contains water. A total amount of the water to be contained in the surface crosslinking agent solution is preferably in a range from 0.5 part by mass to 20 parts by mass, and more preferably in a range from 0.5 part by mass to 10 parts by mass, relative to 100 parts by mass of the water absorbent resin before an addition treatment. It should be noted that the water includes crystalline water, hydrated water, or the like of the surface crosslinking agent.

A hydrophilic organic solvent may be used in the surface crosslinking agent solution. A used amount of the hydrophilic organic solvent is preferably more than 0 part by mass and not more than 10 parts by mass, and more preferably more than 0 part by mass and not more than 5 parts by mass, relative to 100 parts by mass of the water absorbent resin before the addition treatment. An example of the hydrophilic organic solvent is a $C_1$-$C_4$ primary alcohol. Preferable examples of the hydrophilic organic solvent include a $C_2$-$C_3$ primary alcohol, lower ketones whose carbon number is 4 or lower, such as acetone, and the like. A more preferable example of the hydrophilic organic solvent is volatile alcohols, in particular, having a boiling point of lower than 150° C., more preferably lower than 100° C. This is because the volatile alcohols evaporate during a surface-crosslinking treatment, and therefore no residue will remain.

Specific examples of the hydrophilic organic solvent encompass: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly)ethylene glycol; amides such as epsilon-caprolactam and N,N-dimethylformamide; sulfoxides such as dimethyl sulfoxide; polyhydric alcohols such as polyoxypropylene and oxyethylene-oxypropylene block copolymers; and the like.

When the surface crosslinking agent solution is mixed with the water absorbent resin, a water-insoluble fine particle and/or a surfactant may be added within a range which does not interfere with the effect of the present invention. Specifically, the water-insoluble fine particle and the surfactant can coexist in an amount of more than 0 part by mass and not more than 10 parts by mass, preferably more than 0 part by mass but not more than 5 parts by mass, and more preferably more than 0 part by mass but not more than 1 part by mass, relative to 100 parts by mass of the water absorbent resin before the addition treatment. As the surfactant etc., used is a surfactant etc. disclosed in U.S. Pat. No. 7,473,739, etc.

A concentration of a surface crosslinking agent in the surface crosslinking agent solution is appropriately determined. A total amount of the above various surface crosslinking agents used in all of a plurality of addition treatments is in a range from 1 mass % to 80 mass %, more preferably in a range from 5 mass % to 60 mass %, still more preferably in a range from 10 mass % to 40 mass %, and particularly preferably in a range from 15 mass % to 30 mass % of an aqueous solution, from the viewpoint of physical properties. It should be noted that the surface crosslinking agent solution contains the hydrophilic organic solvent and/or other component(s) as residues.

A temperature of the surface crosslinking agent solution is appropriately determined based on solubility of the surface crosslinking agent to be used, viscosity of the surface crosslinking agent solution, etc. The temperature of the surface crosslinking agent solution is preferably in a range from −10° C. to 100° C., more preferably in a range from 5° C. to 70° C., still more preferably in a range from 10° C. to 65° C., and particularly preferably in a range from 25° C. to 50° C. A high temperature is not preferable because, before the surface crosslinking agent solution is mixed or reacted with the water absorbent resin, the high temperature can cause (i) hydrolysis of a cyclic surface crosslinking agent (e.g. degradation from ethylene carbonate into ethylene glycol, degradation from oxazolidinone into ethanolamine) and (ii) deterioration in mixability due to, for example, volatilization of the water and the hydrophilic organic solvent. A too low temperature is neither preferable because the too low temperature causes (i) coagulation of the surface crosslinking agent solution and (ii) precipitation of the surface crosslinking agent.

(Surfactant)

A polyacrylic acid (salt)-based water absorbent resin, a water absorbent resin particle, and a water absorbent resin material each may contain a surfactant. It is preferable that the production method of the present invention include a step of mixing the surfactant in any of the steps.

Coating, with the surfactant, surfaces of the water absorbent resin, the water absorbent resin particle, and the water absorbent resin material of the present invention enables each of the water absorbent resin particle and the water absorbent resin material to attain a high water absorbing speed and a high liquid permeability. It should be noted that the surfactant is not particularly limited. Examples of the surfactant encompass surfactants disclosed in International Publication No. WO97/017397 and U.S. Pat. No. 6,107,358, i.e. a nonionic surfactant, an anionic surfactant, a cationic surfactant, an amphoteric surfactant, and the like. These surfactants may be polymerizable or reactive with an acrylic acid (salt)-based monomer or a water absorbent resin. As a specific compound used are compounds described in (2-1) of Patent Literatures 22 and 23.

Kinds of surfactant to be used and a used amount of the surfactant are determined as appropriate so that, preferably surface tension is preferably not less than 60 [mN/m], more preferably not less than 65 [mN/m], still more preferably not less than 67 [mN/m], particularly preferably not less than 70 [mN/m], and most preferably not less than 72 [mN/m], and so that upper limit of the surface tension is typically not more than 75 [mN/m]. The surface tension can be measured according to the method described in International Publication No. WO2011/078298.

Specifically, the used amount of the surfactant is in a range from 0 part by mass to 0.5 part by mass, still more preferably in a range from 0.00001 part by mass to 0.1 part by mass, and particularly preferably in a range from 0.001 part by mass to 0.05 part by mass, relative to the water absorbent resin. In terms of effect, among these surfactants, it is preferable to use the anionic surfactant, the nonionic surfactant, or a silicone surfactant. It is more preferable to use the nonionic surfactant or the silicone surfactant.

(Use of Acid or Base in Combination with Surface Crosslinking Agent Solution)

For the purpose of promoting reaction and uniform mixing of the surface crosslinking agent, the surface crosslinking agent solution may further contain an acid or a base in addition to the organic surface crosslinking agent, the hydrophilic organic solvent, the surfactant, and the water-insoluble fine particle.

As the acid or the base used is an organic acid or a salt thereof, an inorganic acid or a salt thereof, or an inorganic base. An appropriate used amount of the acid or the base is in a range from 0 part by mass to 10 parts by mass, more preferably in a range from 0.001 part by mass to 5 parts by mass, and still more preferably in a range from 0.01 part by mass to 3 parts by mass, relative to 100 parts by mass of the water absorbent resin before the addition treatment. The organic acid is, for example, a $C_1$-$C_6$, more preferably $C_2$-$C_4$, water-soluble organic acid, water-soluble saturated organic acid, particularly saturated organic acid containing a hydroxyl group.

Other examples of the acid or the base encompass: non-crosslinkable, water-soluble inorganic bases (preferably, alkali metal salt, ammonium salt, hydroxide of alkali metal, and ammonia or hydroxide thereof); an irreducible-alkali-metal-salt pH buffer (preferably hydrogencarbonate, dihydrogen phosphate, hydrogen phosphate, etc.); and the like.

(Method of Adding a Surface Crosslinking Agent Solution)

Through an addition treatment, the surface crosslinking agent is added to a water absorbent resin. A method of carrying out the addition treatment is not particularly limited, and includes (i) a method of immersing a water absorbent resin into a hydrophilic organic solvent that contains a surface crosslinking agent to allow the water absorbent resin to adsorb the surface crosslinking agent, (ii) a method of spraying or dropping a surface crosslinking agent solution directly to a water absorbent resin and mixing them; and like methods. From the viewpoint of uniformly adding a predetermined amount of surface crosslinking agent to a water absorbent resin, the latter method is more preferable. In order to uniformly add the surface crosslinking agent, it is preferable to carry out the addition treatment while the water absorbent resin is being stirred. It is still more preferable to spray the surface crosslinking agent.

The addition treatment may be carried out by (i) simultaneously adding, with, e.g., different spray nozzles, two or more kinds of surface crosslinking agent solutions which are different in composition, respectively or (ii) adding only one kind of surface crosslinking agent solution. Note here that "two or more kinds of surface crosslinking agent solutions which are different in composition" include (i) two or more kinds of surface crosslinking agent solutions which are different in kinds of and/or amount of a crosslinking agent, (ii) two or more kinds of surface crosslinking agent solutions which are identical in kinds of crosslinking agent but different in composition of solutions, and the like. From the viewpoint of uniformity etc., one kind of surface crosslinking agent solution, i.e., a single composition is preferable. Even in a case of the single composition, a plurality of spray nozzles may be used in consideration of (i) size and throughput of an addition treatment apparatus, (ii) spraying angle of a spray nozzle, etc.

Preferable examples of the addition treatment apparatus (hereinafter also referred to as "mixing apparatus) encompass a cylindrical mixer, a double-wall conical mixer, a V-shaped mixer, a ribbon mixer, a screw type mixer, a fluidization type furnace, a rotary disc mixer, an air mixture, a double-arm kneader, an internal mixer, a pulverizing type kneader, a rotating mixer, a screw-type extruder, a Turbulizer, a ploughshare mixer, and the like. For large-scale production such as commercial production, a continuous mixing apparatus is preferable. For a plurality of addition treatments, the same mixing apparatus or different mixing apparatuses may be used.

The water absorbent resin used in the addition treatment is preferably heated and kept warm. A temperature of the water absorbent resin is preferably in a range from 30° C. to 100° C., more preferably in a range from 35° C. to 80° C., and still more preferably in a range from 40° C. to 70° C. A low temperature is not preferable because precipitation of the surface crosslinking agent, moisture absorption of the water absorbent resin, etc., cause insufficient or non-uniform addition of the surface crosslinking agent. In a case where the temperature of the water absorbent resin is extremely high, particularly higher than the boiling point of water, for example, water evaporates from a surface crosslinking agent aqueous solution, which may result in, e.g., precipitation of the surface crosslinking agent.

(2-8) Surface Crosslinking Step

This step is a step of carrying out a heat treatment so as to carry out a crosslinking treatment of a surface of a water absorbent resin or a vicinity of the surface, in order to improve absorption capacity under load of and liquid permeability of the water absorbent resin. The surface crosslinking step can be carried out simultaneously with or after the surface crosslinking agent addition step. The surface crosslinking step is more preferably carried out after the surface crosslinking agent addition step. The surface crosslinking step may be carried out once or may be carried out more than once under the same condition or under different conditions.

(Heating Apparatus)

A suitable example of a heating apparatus used in the present invention is a continuous-type or batch-type heating apparatus in which a publicly-known drier or heating furnace is provided with a gas discharge mechanism and/or a gas supply mechanism for attaining a predetermined atmosphere, and more preferably the continuous-type heating apparatus.

A heating method of the heating apparatus is suitably conductive heat transfer, radiative heat transfer, hot-air heat transfer, or dielectric heating, more preferably the conductive heat transfer and/or the hot-air heat transfer, and still more preferably the conductive heat transfer.

A so-called control temperature of the heating apparatus needs only to be a temperature which can be increased to a temperature (later described) to which the water absorbent resin is heated, and needs not to be held constant from the beginning to the end of the surface crosslinking step. Note, however, that, in order to prevent partial overheating etc., the control temperature of the heating apparatus is preferably in a range from 100° C. to 300° C., more preferably in a range from 120° C. to 280° C., still more preferably in a range from 150° C. to 250° C., and particularly preferably in a range from 170° C. to 230° C., for not less than 70% of, more preferably not less than 90% of, particularly preferably a substantially entire of a time period from the beginning to the end of the surface crosslinking step.

In order to enhance heating efficiency and to carry out a uniform heat treatment, it is more preferable to use a heating apparatus having a stirring mechanism for continuously stirring a target to be heated and/or a fluidizing mechanism for continuously fluidizing a target to be heated. A method of stirring and/or fluidizing the target to be heated is preferably groove-shaped stirring, a screw type, a rotary type, a disc type, a kneading type, a fluidized-bed type, and the like, and more preferably a stirring method using a stirring blade (paddle), and a stirring method based on movement of a heat transfer surface itself such as a stirring method using a rotary retort furnace. It should be noted that the stirring mechanism and/or the fluidizing mechanism need not to be used in a case where throughput is small, for example, in a case where a material to be dried has a thickness of less than 1 cm. This is because the stirring mechanism and/or the fluidizing mechanism are/is used for the purpose of carrying out a uniform heat treatment.

The heating apparatus may have a gas discharge mechanism for discharging vapor generated from a target to be heated, and also can control atmospheric dew point and temperature of a heating section (inside of the heating apparatus) by adjusting the gas discharge mechanism, for example, by adjusting amount of gas to be discharged. It should be noted that the heating section is not a so-called heat source such as a heater or an induction coil but a place to increase a temperature of the target to be heated.

It is preferable that a pressure of gas in the heating section be slightly lower than a normal atmospheric pressure. Such a pressure differential is preferably in a range from 0 kPa to −10 kPa, more preferably in a range from 0 kPa to −5 kPa, and still more preferably in a range from 0 kPa to −2 kPa, relative to atmospheric pressure.

In a case of industrial continuous production, it is possible to use a batch-type or continuous-type heating apparatus having the above mechanism(s).

For the batch-type heating apparatus used is (i) a method of statically leaving a target to be heated in one or more trays or the like so as to be distributed substantially uniformly, (ii) a method of filling a single bath or a plurality of baths with a target to be heated and then heating the target to be heated while stirring with a stirring blade etc., (iii) a fluidized bed, or the like. For the continuous-type heating apparatus used is (i) a method of substantially uniformly distributing a target to be heated onto a belt or a plurality of trays and then conveying the target to be heated on the belt or the plurality of trays, (ii) a method of conveying a target to be heated while stirring with a stirring blade, a screw, etc., (iii) a method of conveying a target to be heated with an inclined heating surface, or like method.

More specifically, the heating apparatus is particularly preferably a conductive heat transfer type heating apparatus which has a stirring mechanism and uses pressurized steam (high-pressure steam) as a heat source. Furthermore, in order to efficiently perform continuous production, the heating apparatus preferably has a slope (which tilts downward at an angle of more than 0 degree relative to a horizontal plane) which allows a target to be heated to naturally flow downward toward an outlet. If a downward tilt angle of the slope is too large, it may cause variation in heating time. For this reason, the slope of the heating apparatus has a tilt angle preferably of more than 0 degree and not more than 20 degrees, and still more preferably of more than 0 degree and not more than 10 degrees, relative to the horizontal plane.

It should be noted that, in a case where addition treatments are carried out before and after a heat treatment, respectively, these addition treatments may be carried out with one and the same apparatus or with respective different apparatuses. Particularly, in a case where a continuous-type production apparatus is used, it is sometimes preferable in terms of production efficiency that one and the same apparatus be used to carry out both the addition treatment before heating and the heat treatment, and another apparatus be used to carry out the addition treatment after heating.

In order to control atmospheric dew point and temperature (later described), the aforementioned amount of gas to be discharged, temperature of gas to be supplied, flow rate, dew point, etc. need only to be appropriately controlled, taking into account (i) heat transfer from a wall surface of the heating apparatus or from a water absorbent resin and (ii) rise in dew point due to water vapor generated from the water absorbent resin in the heating apparatus.

(Atmospheric Dew Point and Temperature)

Atmospheric dew point and temperature in the surface crosslinking step means atmospheric dew point and temperature of gas that exists in an upper space above a target to be heated in the heating section of the heating apparatus.

Examples of a method of adjusting the dew point include (i) a method of using, as the gas to be supplied, steam, dry air, nitrogen, helium, argon, and/or dried air, and (ii) a method of using water vapor generated from water contained in a water absorbent resin due to heating in the surface crosslinking step. Specific examples of the method of adjusting the dew point include (i) a method of providing, for the heating apparatus, a device for measuring the dew point, introducing the gas to be supplied as appropriate, and adjusting the dew point and (ii) a method of adjusting the dew point, for example, by changing the flow rate and pressure of the gas to be discharged. In the present invention, a plurality of methods may be appropriately used in combination, if necessary.

The atmospheric dew point is controlled preferably in a range from 45° C. to 100° C., more preferably in a range from 50° C. to 98° C., and still more preferably in a range from 55° C. to 95° C.

In order to prevent condensation in the heating section, the atmospheric temperature is preferably a temperature of not lower than the dew point. The atmospheric temperature is specifically in a range from 100° C. to 300° C., more preferably in a range from 100° C. to 250° C., and still more preferably in a range from 100° C. to 230° C. It should be noted that the atmospheric dew point is as described above.

The atmospheric dew point and temperature each vary depending upon a location inside the heating section and with lapse of a treatment time. However, the atmospheric dew point and temperature are particularly preferably controlled to fall within given ranges in the apparatus (it is preferable that the atmospheric dew point and temperature do not fall outside the above respective ranges, and ranges of variation in the atmospheric dew point and temperature (difference between an upper limit and a lower limit of the atmospheric dew point) fall preferably within 20° C., more preferably within 10° C., still more preferably within 5° C., and particularly preferably within 2° C.).

The heat treatment in the surface crosslinking step needs only to be such that a maximum temperature of a water absorbent resin that is a target to be heated in the surface crosslinking step is higher than an atmospheric dew point of a gas. The maximum temperature is preferably in a range from 100° C. to 300° C., more preferably in a range from 150° C. to 250° C., and particularly preferably in a range from 170° C. to 230° C. The maximum temperature of not lower than 100° C. is preferable because covalent binding for surface crosslinking is sufficiently formed. The maximum temperature of not higher than 300° C. is preferable because a water absorbent resin is unlikely to deteriorate. A time period of the heat treatment is not particularly limited, provided that the above temperature condition is satisfied. However, the time period of the heat treatment is usually in a range from 1 to 120 minutes, and more preferably in a range from 5 to 60 minutes.

Variation in solid content (mass %) before and after surface crosslinking (solid content of a water absorbent resin before the surface crosslinking agent addition step (solid content of dried water absorbent resin)−solid content of the water absorbent resin after the surface crosslinking) may be increased or decreased. In order to maximally bring about the effect of the present invention, however, it is preferable that the variation be not more than −2 mass % and/or the solid content of the water absorbent resin after the surface crosslinking be less than 2 mass %.

Furthermore, for the purpose of preventing an excessive crosslinking reaction and improving ease of handling in a subsequent step, a water absorbent resin taken out of the heating apparatus may be cooled as appropriate to a temperature of preferably lower than 100° C., more preferably in a range from 0° C. to 95° C., and still more preferably in a range from 40° C. to 90° C.

(2-9) Water-Soluble or Water-Dispersible Polymer Addition Step

This step is a step of adding a water-soluble or water-dispersible polymer, is preferably carried out after the drying step, and may be carried out simultaneously with the surface crosslinking agent addition step. In a case where a water-dispersible polymer is used, it is preferable to carry out a heating step of heating a water absorbent resin to 100° C. or higher after the water-soluble or water-dispersible polymer addition step, and it is more preferable to carry out the heating step of heating the water absorbent resin to 150° C. or higher after the water-soluble or water-dispersible polymer addition step. Note that the surface crosslinking step can be substituted for the heating step. Specifically, for example, (A) the water-soluble or water-dispersible polymer addition step, the surface crosslinking agent addition step, and the surface crosslinking step are carried out in this order after the drying step, (B) the surface crosslinking agent addition step, the water-soluble or water-dispersible polymer addition step, and the surface crosslinking step are carried out in this order after the drying step, (C) after the drying step, the surface crosslinking agent addition step and the water-soluble or water-dispersible polymer addition step are carried out simultaneously, and then the surface crosslinking step is carried out, (D) the surface crosslinking agent addition step, the surface crosslinking step, the water-soluble or water-dispersible polymer addition step, and the heating step are carried out in this order after the drying step, or (E) the water-soluble or water-dispersible polymer addition step, the heating step, the surface crosslinking agent addition step, and the surface crosslinking step are carried out in this order after the drying step. The order (A), (B) or (C) is more preferable. In order to sufficiently attain convenience of a production step and the effect of the present invention, particularly preferable is the order (C) where the water-soluble or water-dispersible polymer addition step is carried out simultaneously with the surface crosslinking agent addition step, and then the surface crosslinking step which also serves as the heating step is carried out.

(Water-Soluble or Water-Dispersible Polymer)

The water-soluble or water-dispersible polymer (hereinafter may be referred to as polymer (C)) used in the present invention has a Log P more preferably in a range from 1.0 to 5.0, and still more preferably in a range from 1.0 to 1.5 or in a range from 3.0 to 3.5.

The Log P can be adjusted based on kinds of and molar ratio of a monomer included in the polymer (C). More preferably, the polymer (C) has at least one group selected from an alkyl ester group, an alkyl ether group, and a benzene ring. Note that the number of kinds of selected group is not limited, provided that the range of the Log P is satisfied.

The polymer (C) has a cation valence preferably in a range from 0 mmol/kg to 0.5 mmol/kg, more preferably in a range from 0 mmol/kg to 0.2 mmol/kg, and still more preferably in a range from 0 mmol/kg to 0.1 mmol/kg (particularly preferably 0 mmol/kg). The cation valence of not more than 0.5 mmol/kg is preferable because coloring (change into yellow) of a water absorbent resin due to heating, deterioration in fluidity due to aggregation of particles, etc. are unlikely to occur. The cation valence is a property derived from N content (e.g., amine structure) in a polymer reactive with acid. The cation valence can be found by means of neutralization titration.

Furthermore, the polymer (C) is more preferably a polymer (i) having a reactive functional group reactive with a carboxyl group and (ii) obtained with use of not less than 5 mol % of a monomer which forms the reactive functional group. Amount of the monomer which forms the reactive functional group is not particularly limited, provided that the Log P and a surface hydrophobic index are satisfied. Examples of the reactive functional group include a hydroxyl group, an epoxy group, an oxazoline group, a carbonate group, an amino group, etc. It is more preferable that the reactive functional group be at least one selected from the hydroxyl group, the oxazoline group, and the carbonate group. Taking into account safety of a resultant water absorbent resin material and absorbent articles made of the resultant water absorbent resin material, it is particularly preferable that the reactive functional group be at least one selected from the hydroxyl group and the carbonate group.

It is considered as follows. Existence of the reactive functional group causes an interaction between the polymer (C) and a carboxyl group that exists on a surface of a water absorbent resin particle. This fixes the polymer (C) to the surface of the water absorbent resin particle. It is also considered as follows. Since the reactive functional group tends to have a high hydrophilicity, balance between hydrophilicity and hydrophobicity of a surface of the water absorbent resin is moderately retained even if a hydrophobic site of the polymer (C) exists, and water absorption performance is not impaired.

The polymer (C) has a mass average molecular weight of preferably not less than 5000, and more preferably not less than 10000. The upper limit of the weight average molecular weight is determined as appropriate. However, the upper limit is typically not more than ten million, and preferably not more than one million.

In a case where a water-dispersible polymer is used as the polymer (C), the polymer (C) in a dispersion solution has an average particle diameter of preferably not more than 300 nm, and more preferably not more than 100 nm. The polymer (C) further has a melting point of preferably not more than 150° C., and more preferably not more than 100° C. The average particle diameter of not more than 300 nm or the melting point of not more than 150° C. is preferable because a uniform dispersion to a surface of the water absorbent resin material is easily caused. A lower limit of the average particle diameter needs only to fall within a range which does not remarkably increase production cost of the polymer (C). Typically, the lower limit is preferably not less than 1 nm, more preferably not less than 10 nm, and still more preferably not less than 30 nm.

The average particle diameter of the polymer in the dispersion solution is measured according to a method such as a dynamic scattering method, a laser diffraction method, a Coulter method, or an image analysis method. In the present invention, it is preferable to measure the average particle diameter with the dynamic scattering method.

The surface hydrophobic index is preferably not more than 10.0, more preferably not more than 8.0, still more preferably not more than 5.0, further still more preferably not more than 3.0, and particularly preferably not more than 2.0. It is possible to determine the surface hydrophobic index by adjusting as appropriate the polymer (C) and an added amount of the polymer (C). Furthermore, the surface hydrophobic index is preferably not less than 0, and more preferably not less than 0.1.

The added amount of the polymer (C) is adjusted depending on the Log P of and the surface hydrophobic index of the polymer (C). Typically, the added amount of the polymer (C) is preferably in a range from 0.001 mass % to 0.2 mass %, more preferably in a range from 0.002 mass % to 0.2 mass %, and still more preferably in a range from 0.002 mass % to 0.1 mass %, relative to the water absorbent resin particle.

The Log P represents hydrophobicity of a water-soluble or water-dispersible polymer, and corresponds to degree of hydrophobicity in a macro structure given to the water absorbent resin material. The surface hydrophobic index is an indicator indicative of hydrophobicity of the surface of the water absorbent resin.

A high Log P increases water-repellency on an interface between the water absorbent resin material and the macro structure like a waterdroplet. This improves liquid permeability. However, a mere improvement of the water-repellency causes deterioration in water absorption performance.

On the other hand, in a case where a partial hydrophilic structure exists even though water-repellency of the whole polymer is high, water can permeate into a site of the water absorbent resin material which site has the partial hydrophilic structure. It is therefore considered that the water absorption performance is not largely impaired.

A specific example of the polymer (C) is a copolymer containing at least one selected from vinyl ester, acrylic acid ester, methacrylic acid ester, and styrene. A particularly preferable example of the polymer (C) is the copolymer containing not less than 5 mol % of, further preferably not less than 10 mol % of, particularly preferably not less than 15 mol % of at least one monomer selected from (i) a copolymerizable monomer having a hydrophilic group such as a hydroxyl group, an oxazoline group, a carbonate group or an amino group, (ii) acrylic acid, (iii) methacrylic acid, and (iv) vinyl sulfonic acid.

Unlike the polymer (C) defined in the present application, polymer compounds described in Patent Literatures 1 through 19 had an excessively low Log P like polyvinylamine (Log P=0.78), polyethyleneimine (Log P=0.63), and polyethylene glycol (Log P=0.98). Alternatively, even if the polymer compounds had a high Log P like polyethylene (Log P=2.88), added amounts of the polymer compounds were inappropriate. This sometimes impaired water absorption performance such as SFC and/or FHA. That is, each of the polymer compounds used in the conventional techniques was added without taking into account hydrophobicity of the polymer compound itself and hydrophilicity of a water absorbent resin to which the polymer compound had been added. It was therefore not possible to obtain a sufficient performance under the presence of a specific water-soluble polyvalent cation. Furthermore, polyamine and polyamide each contained many nitrogen atoms (N), and it was not possible to solve a problem of coloring.

The polymer (C) is preferably added as an aqueous solution and/or an aqueous dispersion solution. The aqueous solution and/or the aqueous dispersion solution more preferably contain(s) a surfactant. An added amount of the surfactant is preferably in a range from 0.0001 mass % to 0.02 mass %, more preferably in a range from 0.0003 mass % to 0.01 mass %, and particularly preferably in a range from 0.0005 mass % to 0.005 mass %, relative to the water absorbent resin to be added. The added amount of the surfactant being not less than 0.0001 mass % is preferable because this added amount brings about a large effect as a lubricant. Furthermore, the added amount of the surfactant being not more than 0.02 mass % is preferable because this added amount is unlikely to cause deterioration in diaper's ability due to deterioration in surface tension.

Kinds of the surfactant are not particularly limited. However, the surfactant is preferably an anionic surfactant, a nonionic surfactant, a cationic surfactant, or an amphoteric surfactant, and more preferably the nonionic surfactant.

(2-10) Water-Soluble Polyvalent Cation Addition Step

In the present invention, it is necessary to add a water-soluble polyvalent cation-containing compound which contains a water-soluble polyvalent cation, in order to add the water-soluble polyvalent cation. A water-soluble polyvalent cation addition step of adding the water-soluble polyvalent cation-containing compound may be carried out simultaneously with the surface crosslinking agent addition step or may be carried out after the surface crosslinking step.

"Carrying out the water-soluble polyvalent cation addition step simultaneously with the surface crosslinking agent addition step" is any of the following cases: (a) a case of adding the water-soluble polyvalent cation-containing compound which has been mixed with the surface crosslinking agent or the surface crosslinking agent solution; (b) a case of adding the water-soluble polyvalent cation-containing compound simultaneously with the surface crosslinking agent or the surface crosslinking agent solution without mixing the water-soluble polyvalent cation-containing compound with the surface crosslinking agent or the surface crosslinking agent solution; and (c) a case of adding the water-soluble polyvalent cation-containing compound at a stage previous to the surface crosslinking agent addition step, or (d) a combination of these cases (a) through (c).

In a case where the surface crosslinking agent addition step and the water-soluble polyvalent cation addition step are each carried out twice or more times, it is more preferable that a last surface crosslinking agent addition step be not carried out after a last water-soluble polyvalent cation addition step, and it is more preferable that an initial water-soluble polyvalent cation addition step be not carried out before an initial surface crosslinking agent addition step. It should be noted that, in a case where the water-soluble polyvalent cation-containing compound is added only once, it is more preferable that the last surface crosslinking agent addition step be not carried out after the water-soluble polyvalent cation addition step, and it is more preferable that the water-soluble polyvalent cation addition step be not carried out before the initial surface crosslinking agent addition step.

For example, (i) the water-soluble polyvalent cation addition step is carried out after the surface crosslinking agent addition step, (ii) the surface crosslinking agent addition step and the water-soluble polyvalent cation addition step are carried out simultaneously, (iii) the surface crosslinking agent addition step and the water-soluble polyvalent cation addition step are carried out simultaneously, and then the water-soluble polyvalent cation addition step is carried out again, or the like.

The surface crosslinking step needs only not to be carried out before the initial surface crosslinking agent addition step. It is preferable that the surface crosslinking step be carried out at least once after the surface crosslinking agent addition step is carried out at least once, and it is more preferable that the surface crosslinking step be carried out once after all surface crosslinking agent addition steps are carried out.

(Water-Soluble Polyvalent Cation-Containing Compound)

The water-soluble polyvalent cation is preferably a bivalent or higher water-soluble polyvalent metal cation, and more preferably a trivalent or higher water-soluble polyvalent metal cation. Examples of the trivalent or higher water-soluble polyvalent metal cation include aluminum cation, zirconium cation, and titanium cation. Among these, the aluminum cation ($Al^{3+}$) is more preferable.

The water-soluble polyvalent cation-containing compound is a compound containing the water-soluble polyvalent cation, and is an ionic compound containing, as a counter, an inorganic anion and/or an organic anion and/or a hydroxyl ion ($OH^-$). Examples of the ionic compound containing the inorganic anion include aluminum sulfate, aluminum chloride, zirconium chloride oxide, zirconium ammonium carbonate, zirconium potassium carbonate, zirconium sulfate, hydroxy zirconium chloride, zirconium nitrate, and the like. Examples of the ionic compound containing the organic anion include aluminum acetate, hydroxy aluminum acetate (mono aluminum acetate), aluminum lactate, zirconium acetate, titanium triethanol aminate, titanium lactate, and the like. Among these, a polyvalent metal cation is more preferably a compound containing aluminum.

Note that the water-soluble polyvalent cation-containing compound may be a basic salt, an acid salt, or a neutral salt.

The water-soluble polyvalent cation-containing compound may be directly mixed in the form of powder with a water absorbent resin. Alternatively, the water-soluble polyvalent cation-containing compound may be mixed in the form of a solution, particularly in the form of an aqueous solution. Further alternatively, the water-soluble polyvalent cation-containing compound may be mixed in the form of being dissolved in a surface crosslinking agent or in an aqueous solution of the surface crosslinking agent. The water-soluble polyvalent cation-containing compound may be used in combination with a stabilizer such as various polyhydric alcohols, boric acid, or tartaric acid.

An added amount of the water-soluble polyvalent cation is preferably in a range from 0.001 part by mass to 1 part by mass, more preferably in a range from 0.005 part by mass to 0.7 part by mass, and still more preferably in a range from 0.01 part by mass to 0.5 part by mass, relative to 100 parts by mass of a water absorbent resin.

Amount of an additive or a liquid permeability improving agent selected from a water-insoluble fine particle and a polyvalent cationic compound is preferably in a range from 0.001 part by mass to 5 parts by mass, more preferably in a range from 0.01 part by mass to 2 parts by mass, and still more preferably in a range from 0.01 part by mass to 1 part by mass, relative to 100 parts by mass of a water absorbent resin to be added. It should be noted that, in a case where the additive or the liquid permeability improving agent is a water-soluble polyvalent metal cation-containing compound, amount of the water-soluble polyvalent metal cation-containing compound is a value converted into amount of polyvalent metal cation from which a counter anion, crystal water, etc. have been removed (for example, in a case of aluminum sulfate, defined in amount of $Al^{3+}$).

The water-soluble polyvalent cation-containing compound may be added twice or more times. For example, in a case where the water-soluble polyvalent cation-containing compound is added twice, a ratio between a first addition and a second addition is in a range from 1:99 to 99:1, and more preferably in a range from 10:90 to 90:10. A ratio falling outside the above ranges is not preferable because it causes a situation extremely close to one-time addition, which reduces effectiveness of a plurality of additions.

In a case where a solvent is used in mixing the water-soluble polyvalent cation-containing compound, the solvent is preferably water or a crosslinking agent aqueous solution. If necessary, a hydrophilic organic solvent (alcohol or polyglycol) or a surfactant may be used in combination so as to improve dispersibility, solubility or mixability. A used amount of the water is appropriately determined according to kinds of additive and an addition method. The used amount is, for example, in a range from 0 part by mass (dry blending) to 50 parts by mass, more preferably in a range from 0.1 part by mass to 10 parts by mass, and still more preferably in a range from 0.5 part by mass to 5 parts by mass, relative to 100 parts by mass of a water absorbent resin.

(2-11) Additive Addition Step of Adding an Additive in Order to Impart Various Functions (Additive Addition Step of Adding Other Additive)

This step is a step of adding other additive in order to impart various functions to a surface-crosslinked water absorbent resin, and includes one step or a plurality of steps. Examples of the other additive include additives such as a liquid permeability improving agent, a deodorant, a perfume, an antimicrobial agent, a foaming agent, a chelating agent, a surfactant, an anti-coloring agent, a pigment, a dye, a fertilizer, an oxidizing agent, a reducing agent, etc. The other additive may be an additive which imparts or improves a function. In the additive addition step, water may be added in order to carry out granulation, water may be added as a solvent of the other additive, and in addition, drying may be carried out after the other additive is added.

A used ratio of the other additive to the surface-crosslinked water absorbent resin, i.e., a water absorbent resin particle is less than 10 mass %, preferably less than 5 mass %, and more preferably less than 1 mass %. The additive addition step of adding the other additive may be carried out simultaneously with or separately from the surface crosslinking step.

(Liquid Permeability Improving Agent)

The liquid permeability improving agent is an additive selected from (i) water-insoluble fine particulate compounds and (ii) polyvalent cationic compounds excluding the water-soluble polyvalent cation-containing compound, and is an additive which improves SFC or free swelling GBP (preferably, improves SFC within a range described below) as compared with a case where no liquid permeability improving agent is used. It should be noted that the term "GBP" is defined in International Publication No. WO2005/016393.

The liquid permeability improving agent serves as a stereoscopic spacer or an electrostatic spacer on a surface of a water absorbent resin. The liquid permeability improving agent causes a resultant water absorbent resin material to bring about effects of "improving liquid permeability (for example, improving SFC (described later) by not less than 1 ($\times 10^{-7}$ $cm^3 \cdot s \cdot g^{-1}$), and still more preferably not less than 10 ($\times 10^{-7}$ $cm^3 \cdot s \cdot g^{-1}$) as compared with the case where no liquid permeability improving agent is used)," "improving Anti-Caking property (for example, improving blocking tendency at moisture absorption (described later) by not less than 1%, and still more preferably by not less than 5%)," "improving gel strength," and "improving free swelling capacity (FSC) (for example, improving FSC (defined by ERT440.2-02) by 0.5 g/g, and still more preferably by not less than 1 g/g)." Besides, depending on kinds of additive, it is possible to bring about effects such as "deodorization/antibacterial activity" and "reduction of a residual surface crosslinking agent," but their effects and intended uses are not particularly limited in the present invention.

"Water-solubility" of the liquid permeability improving agent means that the liquid permeability improving agent dissolves in 100 g of water (25° C.) by not less than 1 g, and still more preferably not less than 5 g. "Water-insolubility" of the liquid permeability improving agent means that the liquid permeability improving agent dissolves in 100 g of water (25° C.) by only less than 1 g, still more preferably less than 0.5 g, and particularly preferably less than 0.1 g.

(Water-Insoluble Fine Particle)

Examples of the water-insoluble fine particle include: water-insoluble fine particulate inorganic powders such as silicon dioxide, titanium dioxide, aluminum oxide, magnesium oxide, zinc oxide, talc, metal phosphate (e.g., calcium phosphate, barium phosphate, and aluminum phosphate), metal borate (e.g., titanium borate, aluminum borate, iron borate, magnesium borate, manganese borate, and calcium borate), silicic acid or salt thereof, clay, diatomaceous earth, zeolite, bentonite, kaolin, hydrotalcite, and activated white clay; and organic fine powders such as calcium lactate and a metal soap (polyvalent metal salt of long chain fatty acid). A volume average particle diameter of the water-insoluble fine particle is preferably not more than 10 μm, and more preferably not more than 1 μm.

The water-insoluble fine particle may be mixed in the form of powder or in the form of a water dispersion (slurry (e.g. colloidal silica)) with a water absorbent resin. Alternatively, the water-insoluble fine particle may be dispersed in a surface crosslinking agent or in an aqueous solution of the surface crosslinking agent, and then mixed with a water absorbent resin.

[3] Physical Properties of Water Absorbent Resin Particle and Water Absorbent Resin Material The following description will discuss physical properties of (i) a water absorbent resin particle such as a polyacrylic acid (salt)-based water absorbent resin particle used in the present invention and (ii) a water absorbent resin material of the present invention.

(3-1) AAP (Absorption Capacity Under Load)

Surface crosslinking after the polymerization is employed as an example to attain the water absorbent resin particle used in the present invention having an absorption capacity under load (AAP) of preferably not less than 20 (g/g), more preferably not less than 22 (g/g), still more preferably not less than 23 (g/g), and particularly preferably not less than 23.5 (g/g), relative to a 0.9 mass % sodium chloride aqueous solution under load of 4.83 kPa. The higher AAP the water absorbent resin particle used in the present invention has, the more preferable it is. However, from the viewpoint of balance between the AAP and other physical properties (e.g., SFC), the AAP of the water absorbent resin particle is preferably not more than 40 (g/g), more preferably not more than 35 (g/g), and still more preferably not more than 30 (g/g). Note that the AAP can be controlled with surface crosslinking, CRC, and a liquid permeability improving agent.

The water absorbent resin material of the present invention has an absorption capacity under load (AAP) of preferably not less than 20 (g/g), more preferably not less than 22 (g/g), still more preferably not less than 23 (g/g), and particularly preferably not less than 23.5 (g/g), relative to a 0.9 mass % sodium chloride aqueous solution under load of 4.83 kPa. The higher AAP the water absorbent resin material of the present invention has, the more preferable it is. However, from the viewpoint of balance between the AAP and other physical properties (e.g., SFC), the AAP of the water absorbent resin material is preferably not more than 40 (g/g), more preferably not more than 35 (g/g), and still more preferably not more than 30 (g/g). Note that the AAP can be controlled with surface crosslinking, CRC, and a liquid permeability improving agent.

(3-2) CRC (Absorption Capacity without Load)

The water absorbent resin particle used in the present invention has an absorption capacity without load (CRC) of not less than 20 (g/g), preferably not less than 23 (g/g), more preferably not less than 25 (g/g), and still more preferably not less than 28 (g/g). A low absorption capacity without load deteriorates efficiency in a case where the water absorbent resin particle is used in hygienic materials such as diapers. The higher CRC the water absorbent resin particle used in the present invention has, the more preferable it is. However, from the viewpoint of balance between the CRC and other physical properties (e.g., SFC), the CRC of the water absorbent resin particle is preferably not more than 60 (g/g), more preferably not more than 50 (g/g), and still more preferably not more than 35 (g/g). The CRC can be controlled by controlling crosslinking density in the polymerization step and/or the surface crosslinking step.

The water absorbent resin material of the present invention has an absorption capacity without load (CRC) of not less than 20 (g/g), preferably not less than 23 (g/g), more preferably not less than 25 (g/g), and still more preferably not less than 28 (g/g). A low absorption capacity without load deteriorates efficiency in a case where the water absorbent resin material is used as hygienic materials such as diapers. The higher CRC the water absorbent resin material of the present invention has, the more preferable it is. However, from the viewpoint of balance between the CRC and other physical properties (e.g., SFC), the CRC of the water absorbent resin material is preferably not more than 60 (g/g), more preferably not more than 50 (g/g), and still more preferably not more than (g/g). The CRC can be controlled by controlling crosslinking density in the polymerization step and/or the surface crosslinking step.

(3-3) SFC (Saline Flow Conductivity)

Saline flow conductivity (SFC) depends on a water absorbent resin composition content (mass %) of a hygienic material. The higher the water absorbent resin composition content is, the higher saline flow conductivity (SFC) is required. From the viewpoint of balance between the SFC and other physical properties (e.g., CRC), the SFC is preferably not more than 1000 ($\times 10^{-7}$ cm$^3$·s·g$^{-1}$). The SFC can be controlled by controlling (i) the aforementioned particle size, (ii) the CRC, and (iii) the crosslinking density during polymerization or during surface crosslinking (particularly, during surface crosslinking).

Surface crosslinking with the polymerization and particle size of a water absorbent resin particle being controlled is employed as an example to attain the water absorbent resin particle used in the present invention having a 0.69 mass % saline flow conductivity (SFC) (liquid permeability of a liquid under load) of preferably not less than 40 ($\times 10^{-7}$·cm$^3$·s·g$^{-1}$), more preferably not less than 80 ($\times 10^{-7}$·cm$^3$·s·g$^{-1}$), still more preferably not less than 100 ($\times 10^{-7}$·cm$^3$·s·g$^{-1}$), and particularly preferably not less than 110 ($\times 10^{-7}$·cm$^3$·s·g$^{-1}$). The water absorbent resin particle used in the present invention having the SFC of not less than 40 ($\times 10^{-7}$ cm$^3$·s·g$^{-1}$) is preferable because (i) the water absorbent resin particle diffuses urine well in a case where the water absorbent resin particle is used in diapers and (ii) utilization efficiency of the water absorbent resin material is high. The upper limit of the SFC of the water absorbent resin particle used in the present invention is not particularly limited. However, from the viewpoint of relation between the SFC and other physical properties (e.g., CRC), the upper limit is preferably not more than 200 ($\times 10^{-7}$ cm$^3 \cdot$s$\cdot$g$^{-1}$), more preferably not more than 160 ($\times 10^{-7}$ cm$^3 \cdot$s$\cdot$g$^{-1}$), and still more preferably not more than 130 ($\times 10^{-7}$ cm$^3 \cdot$s$\cdot$g$^{-1}$).

The water absorbent resin material of the present invention has a 0.69 mass % saline flow conductivity (SFC) (liquid permeability of a liquid under load) of preferably not less than 40 ($\times 10^{-7} \cdot$cm$^3 \cdot$s$\cdot$g$^{-1}$), more preferably not less than 80 ($\times 10^{-7} \cdot$cm$^3 \cdot$s$\cdot$g$^{-1}$), still more preferably not less than 100 ($\times 10^{-7} \cdot$cm$^3 \cdot$s$\cdot$g$^{-1}$), and particularly preferably not less than 110 ($\times 10^{-7} \cdot$cm$^3 \cdot$s$\cdot$g$^{-1}$). The water absorbent resin material of the present invention having the SFC of not less than 40 ($\times 10^{-7}$ cm$^3 \cdot$s$\cdot$g$^{-1}$) is preferable because (i) the water absorbent resin material diffuses urine well in a case where the water absorbent resin material is used in diapers and (ii) utilization efficiency of the water absorbent resin material is high. The upper limit of the SFC of the water absorbent resin material of the present invention is not particularly limited. However, from the viewpoint of relation between the SFC and other physical properties (e.g., CRC), the upper limit is preferably not more than 200 ($\times 10^{-7}$ cm$^3 \cdot$s$\cdot$g$^{-1}$), more preferably not more than 160 ($\times 10^{-7}$ cm$^3 \cdot$s$\cdot$g$^{-1}$), and still more preferably not more than 130 ($\times 10^{-7}$ cm$^3 \cdot$s$\cdot$g$^{-1}$).

(3-4) Extr.

Extr. (water soluble component) of the water absorbent resin particle used in the present invention is preferably in a range from 5 mass % to 20 mass %, more preferably in a range from 5 mass % to 18 mass %, and still more preferably in a range from 5 mass % to 15 mass %. The water absorbent resin particle whose Extr. is not more than 20 mass % has excellent gel strength and liquid permeability.

The Extr. of the water absorbent resin particle used in the present invention can be controlled as appropriate with the aforementioned internal crosslinking agent or the like. The water absorbent resin particle whose Extr. is not less than 5 mass % is preferable because (i) the water absorbent resin particle can be obtained without use of an excessively large amount of internal crosslinking agent, (ii) it is possible to prevent increase in cost and occurrence of a remaining crosslinking agent (beyond the limit of detection), and (iii) the CRC is not remarkably reduced.

Extr. (water soluble component) of the water absorbent resin material of the present invention is preferably in a range from 5 mass % to 20 mass %, more preferably in a range from 5 mass % to 18 mass %, and still more preferably in a range from 5 mass % to 15 mass %. The water absorbent resin material whose Extr. is not more than 20 mass % has excellent gel strength and liquid permeability. Furthermore, the water absorbent resin material whose Extr. is not more than 20 mass % is preferable because, in a case where the water absorbent resin material is used as a water absorber of diapers or the like, the water absorbent resin material less returns a liquid which has been absorbed to be unabsorbed again (rewet) when pressure is applied to the water absorber.

The Extr. of the water absorbent resin material of the present invention can be controlled as appropriate with the aforementioned internal crosslinking agent or the like. The water absorbent resin material whose Extr. is not less than 5 mass % is preferable because (i) the water absorbent resin material can be obtained without use of an excessively large amount of internal crosslinking agent, (ii) it is possible to prevent increase in cost and occurrence of a remaining crosslinking agent (beyond the limit of detection), and (iii) the CRC is not remarkably reduced.

(3-5) FSR (Free Swell Rate)

"FSR" stands for Free Swell Rate, and means a water absorbing speed (free swell rate). Specifically, "FSR" is speed (unit: [g/g/s]) at which 1 g of a water absorbent resin absorbs 20 g of a 0.90 mass % sodium chloride aqueous solution.

FSR of the water absorbent resin particle used in the present invention is preferably not less than 0.15 g/g/s, more preferably in a range from 0.20 g/g/s to 0.4 g/g/s, and still more preferably in a range from 0.25 g/g/s to 0.35 g/g/s. The water absorbent resin particle used in the present invention having the FSR of not less than 0.15 g/g/s is preferable because, in a case where the water absorbent resin particle is used as a water absorber of diapers or the like, the water absorbent resin particle has a sufficient water absorbing speed, and less returns a liquid which has been absorbed to be unabsorbed again (rewet). The water absorbent resin particle having the FSR of not more than 0.4 g/g/s is preferable because other physical properties (e.g., SFC) do not deteriorate.

FSR of the water absorbent resin material of the present invention is preferably not less than 0.15 g/g/s, more preferably in a range from 0.20 g/g/s to 0.4 g/g/s, and still more preferably in a range from 0.25 g/g/s to 0.35 g/g/s. The water absorbent resin material of the present invention having the FSR of not less than 0.15 g/g/s is preferable because, in a case where the water absorbent resin material is used as a water absorber of diapers or the like, the water absorbent resin material has a sufficient water absorbing speed, and less returns a liquid which has been absorbed to be unabsorbed again (rewet). The water absorbent resin material having the FSR of not more than 0.4 g/g/s is preferable because other physical properties (e.g., SFC) do not deteriorate.

(3-6) Fixed Height Absorption (FHA) at a Height of 20 cm

Fixed height absorption (FHA) at a height of 20 cm is a value obtained according to the method described in the specification of US2005/0003191. FHA of the water absorbent resin particle used in the present invention is preferably not less than 20 g/g, more preferably not less than 22 g/g, and still more preferably not less than 24 g/g. The higher the FHA is, the more preferable it is. However, from the viewpoint of balance between the FHA and other physical properties (e.g., SFC), the FHA is preferably not more than 40 (g/g), more preferably not more than 35 (g/g), and still more preferably not more than 30 (g/g). The water absorbent resin particle having the FHA of not less than 20 g/g is preferable because, in a case where the water absorbent resin particle is used in diapers, the water absorbent resin particle absorbs urine well.

FHA of the water absorbent resin material of the present invention is preferably not less than 20 g/g, more preferably not less than 22 g/g, and still more preferably not less than 24 g/g. The higher the FHA is, the more preferable it is. However, from the viewpoint of balance between the FHA and other physical properties (e.g., SFC), the FHA is preferably not more than 40 (g/g), more preferably not more than 35 (g/g), and still more preferably not more than 30 (g/g). The water absorbent resin material having the FHA of not less than 20 g/g is preferable because, in a case where the water absorbent resin material is used in diapers, the water absorbent resin material absorbs urine well.

(3-7) Particle Size Distribution of Water Absorbent Resin Material, and Additive Etc. Which Imparts a Function There is no particular limitation on particle diameters and particle size distributions of the water absorbent resin particle and the water absorbent resin material which are obtained in the present invention. However, it is preferable to obtain a water absorbent resin particle and a water absorbent resin material each having a particle diameter of less than 1 mm, and more preferably the following particle diameter, by sizing particles after adding/mixing a last additive. A particle having a diameter of not more than 1 mm, especially not more than 850 µm is preferable because (i) the particle do not cause to a user uncomfortableness which is caused in a case where a coarse particle is used particularly in a thin hygienic material/absorbent article, and (ii) the particle is unlikely to damage due to abrasion a water impermeable material (a so-called back sheet) constituting an absorbent article, and therefore does not cause leakage of urine or the like in actual use. Hence, it is preferable that a particle of not less than 850 µm be less contained. The particle of not less than 850 µm to be contained is preferably in a range from 0 mass % to 5 mass %, more preferably in a range from 0 mass % to 3 mass %, still more preferably in a range from 0 mass % to 1 mass %, and still more preferably substantially 0 mass %.

On the other hand, a percentage of fine particles having a diameter of less than 150 µm is preferably in a range from 0 mass % to 3.0 mass %, more preferably in a range from 0 mass % to 2.0 mass %, and still more preferably in a range from 0 mass % to 1.5 mass %.

Furthermore, while maintaining the above ranges, particles having a diameter in a range from 150 µm to 850 µm are contained by preferably not less than 95 mass % (upper limit: 100 mass %), more preferably not less than 98 mass %, and still more preferably not less than 99 mass %. Most preferably, all particles are substantially in the range from 150 µm to 850 µm.

The water absorbent resin material to be obtained as a final product through the above steps in the present invention has a mass average particle diameter (D50) (defined by standard sieve classification of the water absorbent resin particle) of preferably not more than 600 µm, more preferably in a range from 200 µm to 550 µm in order to improve its performance, still more preferably in a range from 250 µm to 500 µm, and most preferably in a range from 350 µm to 450 µm.

The water absorbent resin particle used in the present invention has a percentage of particles having a particle diameter of less than 300 µm, the percentage being preferably not less than 10 mass %, more preferably in a range from 10 mass % to 50 mass %, and still more preferably in a range from 10 mass % to 30 mass %. Note that the particle size can be controlled as appropriate with pulverization, classification (before and/or after surface crosslinking), granulation, etc.

The water absorbent resin material of the present invention has a percentage of particles having a particle diameter of less than 300 µm, the percentage being preferably not less than 10 mass %, more preferably in a range from 10 mass % to 50 mass %, and still more preferably in a range from 10 mass % to 30 mass %. Note that the particle size can be controlled as appropriate with pulverization, classification (before and/or after surface crosslinking), granulation, etc.

Examples of an additive which imparts a function include a liquid permeability improving agent, a deodorant, a perfume, an antimicrobial agent, a foaming agent, a chelating agent, a surfactant, an anti-coloring agent, a pigment, a dye, a fertilizer, an oxidizing agent, a reducing agent, and the like. A percentage of the additive to be used relative to a surface-crosslinked water absorbent resin particle is less than 10 mass %, preferably less than 5 mass %, and more preferably less than 1 mass %.

The water absorbent resin material may contain a small amount of water. A moisture content (weight decrease ratio after drying at 180° C. for three hours) of the water absorbent resin material is preferably in a range from 0 mass % to 15 mass %, more preferably in a range from 0.1 mass % to 10 mass %, and still more preferably in a range from 0.5 mass % to 8 mass %.

[4] Use Etc. Of Particulate Water Absorbent Resin Material

It is possible to obtain, within the scope of the present invention, a well-balanced water absorbent resin material which maintains a desired absorption capacity and has an excellent liquid permeability. Particularly a particle having a particle diameter of less than 150 µm is preferably contained as less as possible. This is because the particle not only deteriorates liquid permeability but also probably exerts an adverse effect such as generation of dust in an environment where the water absorbent resin material is used as a raw material to produce absorbent articles.

The water absorbent resin material of the present invention preferably contains, in addition to a surface-crosslinked water absorbent resin particle, (i) a liquid permeability improving agent or (ii) an additive selected from water-insoluble fine particulate compounds and cationic compounds. The water absorbent resin material of the present invention may further contain an additive(s) such as a deodorant, a perfume, an antimicrobial agent, a foaming agent, a chelating agent, a surfactant, an anti-coloring agent, a pigment, a dye, a fertilizer, an oxidizing agent, and a reducing agent so that a function is imparted or improved. A percentage of these additives to be used relative to a total amount of water absorbent resin particles and water-soluble polyvalent metal salt particles is less than 10 mass %, preferably less than 5 mass %, and more preferably less than 1 mass %.

The water absorbent resin material of the present invention maintains high liquid permeability and FHA (and further, water absorbing speed) as compared to the conventional techniques, and is therefore used as hygienic materials such as disposable diapers, sanitary napkins, incontinence pads, medical pads, etc., particularly disposable diapers. Particularly, the water absorbent resin material of the present invention maintains high liquid permeability and FHA, and is therefore used as a hygienic material, and provides a superabsorbent hygienic material having excellent liquid dispersibility and suction as a hygienic material. That is, the present invention also provides a hygienic material containing the water absorbent resin material of the present invention. The present invention further provides use of the water absorbent resin material of the present invention as a hygienic material.

In a case where the water absorbent resin material of the present invention is used as the hygienic materials, the water absorbent resin material preferably includes (i) a liquid-permeable top sheet located adjacent to a body of a user, (ii) a liquid-impermeable back sheet located away from the body of the user but adjacent to clothing of the user, and (iii) a water absorber located between the top sheet and the back sheet. The water absorber may be made up of two or more layers, or may be used in combination with a pulp layer etc.

In the case where the water absorbent resin material of the present invention is used as the hygienic materials, a gel having absorbed liquid is unlikely to cause a so-called gel blocking, and a space between gel particles is not blocked due to close contact of gels. Hence, even in a case where the water absorbent resin material is used at high concentration in an absorbent body of a diaper etc., urine and a bodily fluid having been discharged for the second or subsequent time can be dispersed into the absorbent body without being stuck on a surface of the absorbent body, and can be distributed throughout the water absorbent resin material inside the absorbent body.

That is, the present application encompasses the following invention.

The inventors of the present invention made a diligent study in order to attain the object, and found that a water absorbent resin material is preferable which includes:

(A) a water absorbent resin particle having a carboxyl group;

(B) a covalent surface crosslinking agent in which the number of carbons is not more than 10;

(C) 0.001 mass % to 0.2 mass % of a water-soluble or water-dispersible polymer whose Log P defined by Expression 1 is not less than 1.0; and (D) 0.001 mass % to 1 mass % of a water-soluble polyvalent cation, the water absorbent resin material having not less than 20 g/g of a fixed height absorption (FHA) at a height of 20 cm,

[Mathematical Expression 4]

$$\text{Log}P = \sum_{i=1}^{n} (VM\text{Log}P(i) \times MR(i)) \quad \text{(Expression 1)}$$

where VM Log P(i) is a calculation value of an "n-octanol/water partition coefficient", at 25° C., of a virtual monomer unit (Virtual Monomer (VM)) in which both ends of a polymer repeating unit (i) are methylated, and MR(i) is a "molar ratio (Mol Ratio (MR))" of the polymer repeating unit (i).

The object can be attained even by the water absorbent resin material including the above (A) through (D) and having an absorption capacity under load of 4.83 kPa of not less than 20 g/g.

As the above (A) preferable is a polyacrylic acid-based water absorbent resin particle whose main component is (meth)acrylic acid and/or a salt thereof.

Note that the above (B) through (D) may react with part or all of the (A), or may be a mixture in which the (B) through (D) can be separated from one another. Furthermore, the (B) through (D) preferably exist on a surface of the (A). Whether or not the (B) through (D) exist on the surface of the (A) can be determined, for example, by directly analyzing the surface of the water absorbent resin particle or a surface of the water absorbent resin material according to various methods, or by analyzing powder obtained, for example, by grinding the surface.

It is preferable that the water absorbent resin material has a surface hydrophobic index defined by Expression 2, the surface hydrophobic index being in a range from 0 to 10. It is further preferable that the surface hydrophobic index is in a range from 0.1 to 10. Note that MS Log P(i) is a multiplication value obtained by multiplying a Log P of each monomer included in the polymer (C) by a molar fraction of the each monomer (MS Log P(i)=Log P(i)×MR(i)).

[Mathematical Expression 5]

$$\text{Surface Hydrophobic Index} = \sum_{i=1}^{n} (MS\text{Log}P(i)) \times \text{added amount} \quad \text{(Expression 2)}$$

of the polymer $(C) \times 100$

It is preferable that the polymer (C) have at least one selected from an alkyl ester group, an alkyl ether group, and a benzene ring. The number of the at least one is not limited, provided that the Log p and the surface hydrophobic index are satisfied. It is more preferable that the polymer (C) contains, as a constituent monomer, at least one selected from vinyl ester, acrylic acid ester, methacrylic acid ester, and styrene. Furthermore, it is more preferable that the polymer (C) contain not less than 10 mol % of the constituent monomer.

The polymer (C) has a cation valence preferably in a range from 0 mmol/kg to 0.5 mmol/kg, and more preferably in a range from 0 mmol/kg to 0.2 mmol/kg. The cation valence of the polymer (C) being not more than 0.5 mmol/kg is preferable because (i) coloring (change into yellow) of a water absorbent resin due to heating, (ii) deterioration in fluidity due to aggregation of particles, etc., are unlikely to occur.

The polymer (C) has a mass average molecular weight of preferably not less than 5000, and still more preferably not less than 10.000.

The polymer (C) more preferably has a reactive functional group reactive with a carboxyl group, and contains not less than 5 mol % of a monomer which forms the reactive functional group. No particular limitation is placed, provided that the Log p and the surface hydrophobic index are satisfied.

The water absorbent resin material contains a surfactant preferably in a range from 0.0001 mass % to 0.02 mass %, more preferably in a range from 0.0003 mass % to 0.01 mass %, and particularly preferably in a range from 0.0005 mass % to 0.005 mass %. The water absorbent resin material containing the surfactant by not less than 0.0001 mass % is preferable because the water absorbent resin material brings about a large effect as a lubricant. The water absorbent resin material containing the surfactant by not more than 0.02 mass % is preferable because diaper performance is not deteriorated due to deterioration in surface tension.

Kinds of the surfactant are not particularly limited. However, the surfactant is preferably an anionic surfactant, a nonionic surfactant, a cationic surfactant, an amphoteric surfactant, or like surfactant, and more preferably the nonionic surfactant.

A method for producing the water absorbent resin material of the present invention preferably includes the step of heating, to 100° C. or higher, the above (A) on which surface at least the above (B) and (C) coexist. The method more preferably includes the step of heating, to 150° C. or higher, the above (A) on which surface at least the above (B) and (C) coexist. In a case where the above (A) is heated at an extremely high temperature, heat deterioration is probably caused. Therefore, it is preferable to heat the (A) at 250° C. or lower.

It is preferable in the method that a temperature of a step of adding the water-soluble polyvalent cation (D) be not higher than 90° C. In a case where the water-soluble polyvalent cation (D) is added in the form of an aqueous solution etc., no limitation is placed provided that neither coagulate nor precipitate is generated. The temperature is typically at 0° C. or higher, and preferably at 20° C. or higher.

Moreover, it is preferable in the method that the surface crosslinking agent (B) and the polymer (C) be added through a step of adding a mixture solution that contains (i) the surface crosslinking agent (B) and (ii) the polymer (C).

It is more preferable in the method that the polymer (C) be added through a step of adding an aqueous solution that contains 0.0001 mass % to 0.02 mass % of a surfactant.

EXAMPLES

The following description will more specifically discuss the present invention with reference to Examples. However, the present invention should not be limited by these Examples. For convenience, "part by mass", "liter" and "milliliter", are sometimes simply referred to as "part", "L", and "ml", respectively. Furthermore, "mass %" is sometimes referred to as "wt %".

Physical properties of a water absorbent resin particle and a water absorbent resin material were measured according to the following methods. Unless otherwise specified, the physical properties were measured at room temperature (23° C.) and at a relative humidity of 50RH %.

A water absorbent resin material used as a final product such as a hygienic material has absorbed moisture. Therefore, physical properties of the water absorbent resin material is measured as appropriate after the water absorbent resin material is separated from the final product and then dried at a low temperature under reduced pressure (e.g., under not more than 1 mmHg (1.33 hPa), at 60° C. for 12 hours). All water absorbent resin materials used in Examples and Comparative Examples had a solid content of not less than 94 mass %. The following measurement methods describe an example where a water absorbent resin is measured. The physical properties of the water absorbent resin particle and the water absorbent resin material can also be measured according to methods similar to the measurement methods.

Physical properties described in Examples and the claims of the present invention were calculated according to the EDANA method and the following measurement methods.

"EDANA" and "ERT"

The term "EDANA" stands for European Disposables and Nonwovens Associations. The term "ERT" stands for EDANA Recommended Test Methods, which is the European-standard (actually the global-standard) method of measuring water absorbent resins. Note that, unless otherwise specified, the following measurement is carried out in conformity with a master copy of the ERT (Known Literature: 2002 revised version) in the present invention.

(a) "CRC" (ERT441.2-02)

"CRC" stands for Centrifuge Retention Capacity, and means absorption capacity without load (hereinafter may be referred to as "absorption capacity"). Specifically, the "CRC" means absorption capacity (unit: [g/g]) observed after 0.200 g of a water absorbent resin wrapped in unwoven cloth is allowed to freely swell in a large excess of a 0.9 mass % sodium chloride aqueous solution for 30 minutes and then drained with a centrifugal machine.

(b) "AAP" (ERT442.2-02)

"AAP" stands for Absorption Against Pressure, and means absorption capacity under load. Specifically, the "AAP" means absorption capacity (unit: [g/g]) observed after 0.900 g of a water absorbent resin is allowed to swell in a 0.9 mass % sodium chloride aqueous solution under load of 2.06 kPa (0.3 psi, 21 [g/cm$^2$]) for 1 hour. Note that, though ERT442.2-02 describes "Absorption Under Pressure", "Absorption Under Pressure" is substantially identical to "Absorption Against Pressure". Note also that, in the present invention and Examples, the AAP was measured under load of 4.83 kPa (0.7 psi, 49 [g/cm$^2$]) to which the load of 2.06 kPa was changed.

(c) "Extr." (ERT 470.2-02)

"Extr." stands for Extractables, and means water soluble component. Specifically, "Extr." is a dissolved polymer amount (unit; mass %) obtained by adding 1.000 g of a water absorbent resin to 200 ml of a 0.9 mass % sodium chloride aqueous solution, and then stirring for 16 hours. The dissolved polymer amount is measured by means of pH titration.

(d) "PSD" (ERT420.2-02)

"PSD" stands for Particle Size Distribution, and means a particle size distribution measured by sieve classification. It should be noted that a mass average particle diameter (D50) and a logarithmic standard deviation (σζ) of a particle size distribution are measured by the method as set forth in "(3) Mass-average particle diameter (D50) and logarithmic standard deviation (σζ) of particle diameter distribution" on page 20, lines 11 through 30 of the specification of European Patent EP1594556 B1.

(e) "Residual Monomers" (ERT410.2-02)

"Residual monomers" mean quantity of monomers left in a water absorbent resin (hereinafter referred to as "residual monomers"). Specifically, "Residual Monomers" are a dissolved monomer quantity (unit; ppm) found after adding 1.0 g of a water absorbent resin to 200 ml of a 0.9 mass % sodium chloride aqueous solution, and stirring at 500 rpm for 1 hour. The dissolved monomer quantity is measured by means of high performance liquid chromatography (HPLC). Note that a residual monomer of a water-containing gel-like crosslinked polymer was measured under a condition where a sample and a stirring time were changed to 2 g and three hours, respectively.

(f) "Moisture Content" (ERT430.2-02)

"Moisture Content" means moisture content of a water absorbent resin. Specifically, "Moisture Content" is a value (unit; mass %) calculated from drying loss found by drying 1 g of a water absorbent resin at 105° C. for 3 hours. Note that, in the present invention, a drying temperature was changed to 180° C., one sample was measured five times, and an average of the five measurements was adopted. Furthermore, a value calculated from 100–moisture content (mass %) was regarded as "resin solid content" in the present invention.

(g) "Density" (ERT460.2-02)

"Density" means bulk specific gravity of a water absorbent resin. Specifically, "Density" is weight (unit; [g/ml]) of a water absorbent resin found by introducing 100 g of the water absorbent resin to an apparatus defined by EDANA, and freely dropping the water absorbent resin into a 100 ml container to fill the container.

(h) "Flow Rate" (ERT450.2-02)

"Flow Rate" means flow speed of a water absorbent resin. Specifically, "Flow Rate" is a time (unit; sec) required 100 g of a water absorbent resin which has been introduced into an apparatus defined by EDANA to be discharged from an outlet of a lowest part of the apparatus.

(i) "Liquid Permeability"

"Liquid permeability" in the present invention means degree of flowing of a liquid between particles of a swollen gel under load or without load. The "liquid permeability" is measured typically as SFC (Saline Flow Conductivity) or GBP (Gel Bed Permeability).

(i-1) "Saline Flow Conductivity (SFC)"

"SFC (Saline Flow Conductivity)" is liquid permeability of a water absorbent resin for a 0.69 mass % sodium chloride aqueous solution under load of 2.07 kPa, and is measured in conformity with the SFC test method disclosed in U.S. Pat. No. 5,669,894.

Unless otherwise specified, the unit of the SFC is ($\times 10^{-7} \cdot cm^3 \cdot s \cdot g^{-1}$) in this specification.

(i-2) "GBP"

"GBP" (Gel Bed Permeability) is liquid permeability of a water absorbent resin for a 0.90 mass % sodium chloride aqueous solution wherein the water absorbent resin is under load or allowed to freely swell, and is measured in conformity with the GBP test method disclosed in International Publication No. WO2005/016393.

(j) "FSR"

"FSR" was measured according to the method described in the specification of US2011/0313113.

(k) Fixed Height Absorption (FHA) at a Height of 20 cm

"FHA" was measured in conformity with the measurement method described in the specification of US2005/0003191.

Reference Example 1 (Polymerization)

Into a 2-litter polypropylene container introduced were (i) 421.7 g of acrylic acid, (ii) 2.75 g of polyethylene glycol diacrylate (molecular weight: 523) as an internal crosslinking agent, (iii) 11.60 g of a 2 mass % ethylene diamine tetramethylene phosphonic acid pentasodium salt (EDTMP.5Na) aqueous solution as a chelating agent, (iv) 140.4 g of a 48.5 mass % sodium hydroxide aqueous solution, and (v) 394.2 g of deionized water (ion exchange water). They were mixed, so that a monomer aqueous solution (1) was prepared. The prepared monomer aqueous solution (1) had a peak temperature of 62° C.

The monomer aqueous solution (1) was cooled. When a temperature of the monomer aqueous solution (1) reached 33° C., 211.9 g of a 48.5 mass % sodium hydroxide aqueous solution whose temperature was adjusted to 40° C. was added to the monomer aqueous solution (1), and mixed with the monomer aqueous solution (1), so that a monomer aqueous solution (2) was prepared. A temperature of the prepared monomer aqueous solution (2) was increased by heat of neutralization in a second stage to reach 78° C.

(Polymerization Step)

While 17.55 g of a 4 mass % sodium persulfate aqueous solution was being stirred, 17.55 g of the 4 mass % sodium persulfate aqueous solution was added to the monomer aqueous solution (2) (monomer temperature: 78° C.). Immediately after the addition, the mixture was poured in an atmospheric air open system into a stainless steel vat-type container (bottom surface: 340 mm×340 mm, height: 25 mm, internal surface: coated with Teflon®. The stainless steel vat-type container was heated with a hot plate (NEO HOTPLACE HI-1000, manufactured by Iuchi Seieido Co., Ltd.) so that a temperature of a surface of the container was increased to 80° C.

In 40 seconds after the sodium persulfate aqueous solution was introduced, the monomer aqueous solution started becoming cloudy. A polymerization reaction progressed while (i) generating water vapor and (ii) causing expansion and foaming upward of and in front, back, left, and right directions of a polymerization container. Then, the reactant was shrunk to a size slightly larger than the polymerization container. This series of operations are carried out in an atmospheric air open system. A peak temperature during polymerization was 110° C.

(Gel-Crushing Step)

A water-containing gel-like crosslinked polymer (1) (hydrogel) obtained through the polymerization reaction was divided into 16 pieces, and further crushed with a meat chopper (manufactured by Iizuka Kogyo Co., Ltd., MEAT-CHOPPER TYPE: 12VR-400KSOX, die pore diameter: 9.5 mm), so that a grain-refined hydrogel (1) was obtained. Specifically, 420 g of the hydrogel was put into the meat chopper per minute while 50 g of deionized water whose temperature was adjusted to 90° C. was being added per minute.

(Drying Step, Pulverization Step, and Classification Step)

The grain-refined hydrogel (1) was dried with hot air at 180° C. for 40 minutes. The dried obtained through this operation was pulverized with a roll mill (manufactured by Inoguchi Giken Ltd., WML-type roll crusher), and then classified with a JIS standard sieve having a mesh size of 710 μm. Particles which passed through the JIS standard sieve having the mesh size of 710 μm were further classified with a JIS standard sieve having a mesh size of 150 μm, and particles which passed through the JIS standard sieve having the mesh size of 150 μm were removed, so that a water absorbent resin (a) was obtained. The water absorbent resin (a) obtained through the above series of operations had a mass average particle diameter (D50) of 431 μm and a logarithmic standard deviation (σζ) of particle size distribution of 0.36.

Example 1

Over 100 parts by mass of the water absorbent resin (a) obtained in Reference Example 1 uniformly sprayed was a surface crosslinking agent solution including (i) 0.4 part by mass of ethylene carbonate, (ii) 0.6 part by mass of propylene glycol, (iii) 0.001 part by mass of polyoxyethylene (20) sorbitan monostearate (manufactured by Kao Corporation), (iv) 3 parts by mass of deionized water, and (v) 0.05 part by mass of a water-soluble polymer A (2-isopropenyl-2-oxazoline/ethyl acrylate/methyl methacrylate/methoxy polyethylene glycol acrylate (n=9)=50/22/3/25 mass %, mass average molecular weight: approximately 40.000, cation valence: 0). The water absorbent resin (a) and the surface crosslinking agent solution were mixed. The water absorbent resin (a) with which this surface crosslinking agent was mixed was heat-treated for a given time with a heating apparatus provided with a stirring blade and a jacket (jacket temperature: 210° C.), and then caused to pass through a JIS standard sieve having a mesh size of 850 μm, so that a surface-crosslinked water absorbent resin particle (la) was obtained.

To 100 parts by mass of the surface-crosslinked water absorbent resin particle (la) added was a mixture solution including (i) 0.8 part by mass of a 27 mass % aluminum sulfate aqueous solution (8 mass % based on aluminum oxide), (ii) 0.134 part by mass of a 60 mass % sodium lactate aqueous solution, and (iii) 0.016 part by mass of propylene glycol. After the addition, they were windlessly dried at 60° C. for 30 minutes. The dried particle was caused to pass through a JIS standard sieve having a mesh size of 850 μm, so that a water absorbent resin material (1) was obtained.

Table 1 showed physical properties in Example 1. Note that values of physical properties such as SFC and AAP in Table 1 are based on CRC=27 g/g.

Example 2

Surface crosslinking was carried out in Example 2 according to a similar method except that an added amount of the water-soluble polymer A of Example 1 was changed to 0.1 part by mass, so that a water absorbent resin material (2) was obtained. Table 1 showed physical properties in Example 2.

Example 3

Surface crosslinking was carried out in Example 3 according to the similar method except that the added amount of the water-soluble polymer A of Example 1 was changed to 0.15 part by mass, so that a water absorbent resin material (3) was obtained. Table 1 showed physical properties in Example 3.

Example 4

Surface crosslinking was carried out in Example 4 according to the similar method except that 0.05 part by mass of the water-soluble polymer A of Example 1 was changed to 0.05 part by mass of a water-soluble polymer B (2-isopropenyl-2-oxazoline/methyl methacrylate/ethyl acrylate=85/10/5 mass %, mass average molecular weight: approximately 120.000, cation valence: 0), so that a water absorbent resin material (4) was obtained. Table 1 showed physical properties in Example 4.

Example 5

Surface crosslinking was carried out in Example 5 according to the similar method except that an added amount of the water-soluble polymer B of Example 4 was changed to 0.1 part by mass, so that a water absorbent resin material (5) was obtained. Table 1 showed physical properties in Example 5.

Example 6

Surface crosslinking was carried out in Example 6 according to the similar method except that 0.05 part by mass of the water-soluble polymer A of Example 1 was changed to 0.0025 part by mass of a 40 mass % water-dispersible emulsion C (styrene/butyl acrylate/2-isopropenyl-2-oxazoline/divinylbenzene=58.1/21.8/20.0/0.1 mass %, cation valence: 0) subjected to solid content conversion, so that a water absorbent resin material (6) was obtained. Table 1 showed physical properties in Example 6.

Example 7

Surface crosslinking was carried out in Example 7 according to the similar method except that an added amount of the emulsion C of Example 6 was changed to 0.005 part by mass with solid content conversion, so that a water absorbent resin material (7) was obtained. Table 1 showed physical properties in Example 7.

Example 8

Surface crosslinking was carried out in Example 8 according to the similar method except that the added amount of the emulsion C of Example 6 was changed to 0.01 part by mass with solid content conversion, so that a water absorbent resin material (8) was obtained. Table 1 showed physical properties in Example 8.

Example 9

Surface crosslinking was carried out in Example 9 according to the similar method except that 0.05 part by mass of the water-soluble polymer A of Example 1 was changed to 0.01 part by mass of a 43 mass % water-dispersible emulsion D (styrene/methacrylic acid/butyl methacrylate/butyl acrylate=52.0/14.3/17.7/16.0 mass %) subjected to solid content conversion, so that a water absorbent resin material (9) was obtained. Table 1 showed physical properties in Example 9.

Example 10

Surface crosslinking was carried out in Example 10 according to the similar method except that an added amount of the water-dispersible emulsion D of Example 9 was changed to 0.02 part by mass with solid content conversion, so that a water absorbent resin material (10) was obtained. Table 1 showed physical properties in Example 10.

Comparative Example 1

Surface crosslinking was carried out in Comparative Example 1 according to the similar method except that the water-soluble polymer A of Example 1 was not added, so that a comparative water absorbent resin material (1) was obtained. Table 1 showed physical properties in Comparative Example 1.

Comparative Example 2

Surface crosslinking was carried out in Comparative Example 2 according to the similar method except that the added amount of the water-soluble polymer A of Example 1 was changed to 0.3 part by mass, so that a comparative water absorbent resin material (2) was obtained. Table 1 showed physical properties in Comparative Example 2.

Comparative Example 3

Surface crosslinking was carried out in Comparative Example 3 according to the similar method except that the added amount of the water-dispersible emulsion C of Example 6 was changed to 0.05 part by mass with solid content conversion, so that a comparative water absorbent resin material (3) was obtained. Table 1 showed physical properties in Comparative Example 3.

Comparative Example 4

Surface crosslinking was carried out in Comparative Example 4 according to the similar method except that 0.05 part by mass of the water-soluble polymer A of Example 1 was changed to 0.1 part by mass of a water-soluble polymer E (polyethylene glycol dipropylamine, mass average molecular weight: approximately 10.000, manufactured by Wako Pure Chemical Industries, Ltd.), so that a comparative water absorbent resin material (4) was obtained. Table 1 showed physical properties in Comparative Example 4.

Comparative Example 5

Surface crosslinking was carried out in Comparative Example 5 according to the similar method except that 0.05 part by mass of the water-soluble polymer A of Example 1 was changed to 0.1 part by mass of a water-soluble polymer F (polyethylene glycol acrylate (n=9)/acrylic acid=60/40 mass %, mass average molecular weight: approximately 50.000), so that a comparative water absorbent resin material (5) was obtained. Table 1 showed physical properties in Comparative Example 5.

Comparative Example 6

Surface crosslinking was carried out in Comparative Example 6 according to the similar method except that 0.05 part by mass of the water-soluble polymer A of Example 1 was changed to 0.1 part by mass of KURARAY POVAL PVA613 (polyvinyl alcohol, saponification ratio: 92.5% to 94.5%), so that a comparative water absorbent resin material (6) was obtained. Table 1 showed physical properties in Comparative Example 6. Note that a surface hydrophobic index was calculated at the saponification ratio of 93.5%.

Comparative Example 7

Surface crosslinking was carried out in Comparative Example 7 according to the similar method except that 0.05 part by mass of the water-soluble polymer A of Example 1 was changed to 0.1 part by mass of Catiofast VFH (polyvinylamine, manufactured by BASF), so that a comparative water absorbent resin material (7) was obtained. Table 1 showed physical properties in Comparative Example 7.

Comparative Example 8

Surface crosslinking was carried out in Comparative Example 8 according to the similar method except that 0.05 part by mass of the water-soluble polymer A of Example 1 was changed to 0.1 part by mass of EPOMIN® P-1000 (polyethyleneimine, mass average molecular weight: approximately 70.000, manufactured by NIPPON SHOKUBAI CO., LTD.), so that a comparative water absorbent resin material (8) was obtained. Table 1 showed physical properties in Comparative Example 8.

Comparative Example 9

In Comparative Example 9, surface crosslinking was carried out with only a water-soluble polymer A without using 0.4 part by mass of ethylene carbonate and 0.6 part by mass of propylene glycol which were contained in the surface crosslinking agent of Example 1, and then, aluminum sulfate was added in the same manner as Example 1, so that a comparative water absorbent resin material (9) was obtained. In Comparative Example 9, a covalent surface crosslinking agent (B) in which the number of carbons is not more than 10, essential to the present application, was omitted (0%). CRC extremely slightly decreased, and could not be decreased to 27 g/g shown in Table 1.

Comparative Example 10

In Comparative Example 10, a comparative water absorbent resin material (10) was obtained without adding aluminum sulfate to the surface-crosslinked water absorbent resin particle (la) of Example 1. In Comparative Example 10, a polyvalent metal cation (D) essential to the present application was omitted (0%). Table 1 showed physical properties in Comparative Example 10.

Comparative Example 11

In Comparative Example 11, as a comparative example conforming to Patent Literature 20, surface crosslinking was carried out with only an oxazoline-based polymer. That is, a water absorbent resin particle (to which no aluminum sulfate had been added) obtained by carrying out surface crosslinking with a surface crosslinking agent including 0.2 wt % of the water-soluble polymer A of Comparative Example 9 and 3 wt % of water was regarded as a comparative water absorbent resin material (11). Under the conditions of the present application, however, even if an amount of the oxazoline-based polymer was increased, CRC extremely slightly decreased, and could not be decreased to 27 g/g shown in Table 1.

Comparative Example 12

Surface crosslinking was carried out in Comparative Example 12 according to the similar method except that 0.05 part by mass of the water-soluble polymer A of Example 1 was changed to 0.1 part by mass of polyethylene glycol (molecular weight: 600), so that a comparative water absorbent resin material (12) was obtained. Comparative Example 12 conforms to Patent Literatures 12 through 15. Table 1 showed the result.

TABLE 1

|  | Additive | Added amount wt % | LogP | Surface Hydrophobic Index | SFC | AAP | FSR | FHA | Coloring |
|---|---|---|---|---|---|---|---|---|---|
| Ex. 1 | Water-Soluble Polymer A | 0.05 | 1.07 | 2.25 | 110 | 23.8 | 0.28 | 22.0 | None |
| Ex. 2 | Water-Soluble Polymer A | 0.1 | 1.07 | 4.50 | 116 | 23.8 | 0.29 | 21.6 | None |
| Ex. 3 | Water-Soluble Polymer A | 0.15 | 1.07 | 6.75 | 115 | 23.7 | 0.28 | 21.1 | None |
| Ex. 4 | Water-Soluble Polymer B | 0.05 | 1.08 | 2.31 | 111 | 23.9 | 0.28 | 22.0 | None |
| Ex. 5 | Water-Soluble Polymer B | 0.1 | 1.08 | 4.60 | 114 | 23.8 | 0.27 | 21.8 | None |
| Ex. 6 | Water-Dispersible Emulsion C | 0.0025 | 3.29 | 0.54 | 113 | 23.8 | 0.28 | 22.1 | None |
| Ex. 7 | Water-Dispersible Emulsion C | 0.005 | 3.29 | 1.08 | 114 | 23.7 | 0.27 | 22.0 | None |
| Ex. 8 | Water-Dispersible Emulsion C | 0.01 | 3.29 | 2.16 | 115 | 23.7 | 0.27 | 21.8 | None |
| Ex. 9 | Water-Dispersible Emulsion D | 0.01 | 3.41 | 2.36 | 114 | 23.8 | 0.27 | 21.7 | None |
| Ex. 10 | Water-Dispersible Emulsion D | 0.02 | 3.41 | 4.72 | 115 | 23.7 | 0.26 | 21.3 | None |
| Com. Ex. 1 | (control) | — | 0 | 0.00 | 103 | 23.8 | 0.28 | 22.3 | None |
| Com. Ex. 2 | Water-Soluble Polymer A | 0.3 | 1.07 | 13.00 | 109 | 23.5 | 0.26 | 19.5 | None |
| Com. Ex. 3 | Water-Dispersible Emulsion C | 0.05 | 3.29 | 10.80 | 103 | 23.4 | 0.24 | 19.9 | None |
| Com. Ex. 4 | Water-Soluble Polymer E | 0.1 | 0.98 | −19.00 | 104 | 23.7 | 0.28 | 22.1 | None |
| Com. Ex. 5 | Water-Soluble Polymer F | 0.1 | 0.61 | −2.00 | 99 | 23.7 | 0.29 | 21.8 | None |
| Com. Ex. 6 | Polyvinyl Alcohol | 0.1 | 0.73 | 2.80 | 103 | 23.8 | 0.28 | 22.3 | None |
| Com. Ex. 7 | Polyvinylamine | 0.1 | 0.78 | −2.00 | 106 | 23.7 | 0.28 | 22.1 | Change in yellow |

TABLE 1-continued

| | Additive | Added amount wt % | LogP | Surface Hydrophobic Index | SFC | AAP | FSR | FHA | Coloring |
|---|---|---|---|---|---|---|---|---|---|
| Com. Ex. 8 | Polyethyleneimine | 0.1 | 0.63 | −8.00 | 105 | 23.7 | 0.27 | 22.0 | Change in yellow |
| Com. Ex. 9 | Water-Soluble Polymer A (without Covalent Surface Crosslinking Agent) | 0.05 | 1.07 | 2.25 | — | — | — | — | None |
| Com. Ex. 10 | Water-Soluble Polymer A (without Aluminum Sulfate) | 0.05 | 1.07 | 2.25 | 70 | 24.8 | 0.26 | 23.2 | None |
| Com. Ex. 11 | Water-Soluble Polymer A only | 0.2 | 1.07 | 9.00 | — | — | — | — | None |
| Com. Ex. 12 | Polyethylene Glycol | 0.1 | 0.98 | −0.30 | 102 | 23.7 | 0.28 | 22.0 | None |

Ex.: Example, and Com. Ex.: Comparative Example

Note that Table 1 showed performance in a case where CRC was 27 g/g. Note, however, that, since it was not possible to obtain CRC of 27 g/g in Comparative Examples 9 and 11, Table 1 did not show other physical properties in Comparative Examples 9 and 11.

(Summary)

As shown in Table 1, it was found that it was possible to attain both an improved saline flow conductivity (SFC) and a high FHA by adjusting a structure of a polymer (Log P≥1.0) and an added amount of the polymer (0.001 wt % to 0.2 wt %) within respective specific ranges.

As is clear from a comparison between Examples 1 through 10 (SFC=110 to 115) and Comparative Examples 4 through 6 (SFC=99 to 104) relative to Comparative Example 1 (SFC=103) where no polymer was used, polymers whose Log P is less than 1 cannot bring about an effect of improving liquid permeability (improvement of particularly SFC by approximately 10 points) even if the surface hydrophobic index is not less than 0.

As is clear from a comparison between Examples 1 through 8 (SFC=110 to 115, FSR=0.27 to 0.29, FHA=21.1 to 22.0) and Comparative Examples 2 and 3 (SFC=109 to 103, FSR=0.24 to 0.26, FHA=19.5 to 19.9), even if polymers have Log P of not less than 1, the surface hydrophobic index of not less than 10 (Comparative Examples 2 and 3) not only reduces an effect of improving liquid permeability but also deteriorates water absorption performance such as FSR and FHA as compared to (i) Comparative Example 1 (SFC=103, FSR=0.28, FHA=22.3) where no polymer was used and (ii) Examples 1 through 8. It is found that it is not possible to obtain a water absorbent resin material whose FHA 20 which is a favorable characteristic of the present application.

As is clear from a comparison between Examples 1 through 10 and Comparative Examples 7 and 8, a cationic polymer which Patent Literatures 1 through 4, etc. conventionally report brings about an effect of improving liquid permeability not only brings about no effect of improving liquid permeability when used within the range of this used amount of the cationic polymer (0.001 wt % to 0.2 wt %) but also causes a problem that a color of a water absorbent resin changes into yellow.

As such, it is found that it is possible to attain all of liquid permeability, water absorbing speed and FHA without coloring and odor, by using an extremely small amount of a specific water-soluble or water-dispersible polymer in a surface-crosslinked water absorbent resin which essentially contains a water-soluble polyvalentcation, i.e., by using 0.001 mass % to 0.2 mass % of a water-soluble or water-dispersible polymer whose Log P is not less than 1.0.

Patent Literatures 11 through 14 and 22 through 30 describe, as a conventional technique, a surface-crosslinked water absorbent resin essentially containing a water-soluble polyvalent cation. However, these Patent Literatures do not suggest at all (i) using an extremely small amount of a specific water-soluble or water-dispersible polymer in a surface-crosslinked water absorbent resin essentially containing a water-soluble polyvalent cation and (ii) the effect (of attaining all of an improved liquid permeability, water absorbing speed, and FHA) of the present application brought about by using the extremely small amount of the specific water-soluble or water-dispersible polymer in the surface-crosslinked water absorbent resin.

The present invention is not limited to the description of the above embodiment, and can therefore be modified by a skilled person in the art within the scope of the claims. Namely, an embodiment derived from a proper combination of technical means disclosed in different embodiments is encompassed in the technical scope of the present invention. Moreover, it is possible to obtain a new technical feature from a proper combination of technical means disclosed in different embodiments.

INDUSTRIAL APPLICABILITY

A water absorbent resin material of the present invention is excellent in liquid permeability, absorption capacity, and water absorbing speed, and is less colored. Therefore, with the water absorbent resin material, it is possible to produce excellent hygienic materials such as diapers which less leak liquid and less return a liquid which has been absorbed to be unabsorbed again.

The invention claimed is:

1. A water absorbent resin material, comprising:

(A) a water absorbent resin particle having a carboxyl group;

(B) a covalent surface crosslinking agent in which the number of carbons is not more than 10;

(C) 0.001 mass % to 0.2 mass % of a water-soluble or water-dispersible polymer (C) whose Log P defined by Expression 1 is not less than 1.0; and (D) 0.001 mass % to 1 mass % of a water-soluble polyvalent cation, the water absorbent resin material having not less than 20 g/g of a fixed height absorption (FHA) at a height of 20 cm,

[Mathematical Expression 1]

$$\mathrm{Log}P = \sum_{i=1}^{n}(VM\mathrm{Log}P(i) \times MR(i)) \quad \text{(Expression 1)}$$

where VM Log P(i) is a calculation value of an "n-octanol/water partition coefficient", at 25° C., of a virtual monomer unit (Virtual Monomer (VM)) in which both ends of a polymer repeating unit (i) are methylated, and MR(i) is a "molar ratio (Mol Ratio (MR))" of the polymer repeating unit (i).

2. The water absorbent resin material as set forth in claim 1, wherein an absorption capacity under load of 4.83 kPa is not less than 20 g/g.

3. The water absorbent resin material as set forth in claim 1, further comprising 0.0001 mass % to 0.02 mass % of a surfactant.

4. The water absorbent resin material as set forth in claim 1, wherein the water-soluble or water-dispersible polymer has a cation valence of not more than 0.5 mmol.

5. The water absorbent resin material as set forth in claim 1, wherein the water absorbent resin material has a surface hydrophobic index defined by Expression 2, the surface hydrophobic index being in a range from 0.1 to 10,

[Mathematical Expression 2]

Surface Hydrophobic Index =

$$\sum_{i=1}^{n}(MS\mathrm{Log}P(i)) \times \text{added amount} \quad \text{(Expression 2)}$$

of the polymer (C) × 100 where MS Log P(i) is a multiplication value obtained by multiplying a Log P of each monomer included in the water-soluble or water-dispersible polymer by a molar fraction of the each monomer (MS Log P(i)=Log P(i)×MR(i)).

6. The water absorbent resin material as set forth in claim 5, wherein the surface hydrophobic index is not less than 0.1.

7. The water absorbent resin material as set forth in claim 1, wherein the water-soluble or water-dispersible polymer has at least one selected from an alkyl ester group, an alkyl ether group, and a benzene ring.

8. The water absorbent resin material as set forth in claim 1, wherein the water-soluble or water-dispersible polymer has a mass average molecular weight of not less than 5000.

9. The water absorbent resin material as set forth in claim 1, wherein the water-soluble or water-dispersible polymer contains not less than 5 mol % of a monomer which forms a reactive functional group reactive with a carboxyl group.

10. The water absorbent resin material as set forth in claim 1, wherein a monomer included in the water-soluble or water-dispersible polymer contains at least one selected from vinyl ester, acrylic acid ester, methacrylic acid ester, and styrene.

11. A method for producing a water absorbent resin material,
the water absorbent resin material including:
(A) a water absorbent resin particle having a carboxyl group;
(B) a covalent surface crosslinking agent in which the number of carbons is not more than 10;
(C) 0.001 mass % to 0.2 mass % of a water-soluble or water-dispersible polymer whose Log P defined by Expression 1 is not less than 1.0; and
(D) 0.001 mass % to 1 mass % of a water-soluble polyvalent cation,

[Mathematical Expression 1]

$$\mathrm{Log}P = \sum_{i=1}^{n}(VM\mathrm{Log}P(i) \times MR(i)) \quad \text{(Expression 3)}$$

where VM Log P(i) is a calculation value of an "n-octanol/water partition coefficient", at 25° C., of a virtual monomer unit (Virtual Monomer (VM)) in which both ends of a polymer repeating unit (i) are methylated, and MR(i) is a "molar ratio (Mol Ratio (MR))" of the polymer repeating unit (i),
the method comprising the step of heating, to 100° C. or higher, the water absorbent resin particle (A) on which surface at least the covalent surface crosslinking agent (B) and the water-soluble or water-dispersible polymer (C) coexist.

12. The method as set forth in claim 11, wherein a temperature of a step of adding the water-soluble polyvalent cation is not higher than 90° C.

13. The method as set forth in claim 11, wherein the covalent surface crosslinking agent and the water-soluble or water-dispersible polymer are added through a step of adding a mixture solution that contains (i) the covalent surface crosslinking agent and (ii) the water-soluble or water-dispersible polymer.

14. The method as set forth in claim 11, wherein the water-soluble or water-dispersible polymer is added through a step of adding an aqueous solution that contains 0.0001 mass % to 0.02 mass % of a surfactant.

15. A hygienic material comprising a water absorbent resin material as set forth in claim 1.

* * * * *